(12) United States Patent  
Brinkman et al.

(10) Patent No.: US 9,402,660 B2
(45) Date of Patent: Aug. 2, 2016

(54) SURGICAL INSTRUMENT AND METHOD

(71) Applicant: Warsaw Orthopedic, Inc., Warsaw, IN (US)

(72) Inventors: Jennifer Brinkman, Memphis, TN (US); Larry Thomas McBride, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 292 days.

(21) Appl. No.: 14/018,897

(22) Filed: Sep. 5, 2013

(65) Prior Publication Data

US 2015/0066088 A1 Mar. 5, 2015

(51) Int. Cl.
*A61B 17/58* (2006.01)
*A61B 17/70* (2006.01)

(52) U.S. Cl.
CPC ........... *A61B 17/708* (2013.01); *A61B 17/7077* (2013.01)

(58) Field of Classification Search
CPC ............... A61B 2017/0256; A61B 2017/0262; A61B 17/025; A61B 2017/681
See application file for complete search history.

(56) References Cited

U.S. PATENT DOCUMENTS

| 776,051 | A | 11/1904 | Fruehling |
| 1,920,821 | A | 8/1933 | Wassenaar |
| 4,957,495 | A | 9/1990 | Kluger |
| 5,219,349 | A | 6/1993 | Krag et al. |
| 7,416,553 | B2 | 8/2008 | Patel et al. |
| 7,578,822 | B2 | 8/2009 | Rezach et al. |
| 7,618,424 | B2 | 11/2009 | Wilcox et al. |
| 7,655,008 | B2 | 2/2010 | Lenke et al. |
| 7,794,464 | B2 | 9/2010 | Bridwell et al. |
| 7,914,536 | B2 | 3/2011 | MacDonald et al. |
| 7,922,731 | B2 | 4/2011 | Schumacher et al. |
| 8,157,806 | B2 | 4/2012 | Frigg et al. |
| 8,206,395 | B2 | 6/2012 | McLean et al. |
| 8,277,453 | B2 | 10/2012 | Kave et al. |
| 8,287,546 | B2 | 10/2012 | King et al. |
| 8,394,109 | B2 | 3/2013 | Hutton et al. |
| 2004/0034298 | A1 | 2/2004 | Johnson et al. |
| 2005/0021040 | A1 | 1/2005 | Bertagnoli |
| 2007/0093846 | A1* | 4/2007 | Frigg ................ A61B 17/025 606/90 |
| 2008/0119862 | A1* | 5/2008 | Wicker ............... A61B 17/708 606/99 |
| 2009/0062857 | A1 | 3/2009 | Ramsay et al. |
| 2010/0246923 | A1 | 9/2010 | Nathaniel et al. |
| 2011/0130793 | A1* | 6/2011 | Woolley ............ A61B 17/0206 606/279 |
| 2011/0172662 | A1 | 7/2011 | Keilen |
| 2011/0319939 | A1 | 12/2011 | Kretzer et al. |
| 2012/0071885 | A1 | 3/2012 | Forton et al. |
| 2012/0296171 | A1* | 11/2012 | Lovell ............... A61B 17/0206 600/213 |
| 2013/0245692 | A1* | 9/2013 | Hayes ................. A61B 17/025 606/279 |

(Continued)

FOREIGN PATENT DOCUMENTS

DE 3414374 10/1985
DE 3807346 6/1989

(Continued)

*Primary Examiner* — Eduardo C Robert
*Assistant Examiner* — Julianna N Harvey

(57) ABSTRACT

A surgical instrument includes a first member defining a longitudinal axis. A second member is disposed with the first member and is axially translatable relative to the first member. A first body is connected to the first member and is translatable along an arcuate path relative to the first member. The first body is connected to a first implant support. A second body is connected to the second member and is translatable along an arcuate path relative to the second member. The second body is connected to a second implant support. Systems and methods of use are disclosed.

20 Claims, 18 Drawing Sheets

(56) References Cited

U.S. PATENT DOCUMENTS

2013/0289633 A1* 10/2013 Gleeson .............. A61B 17/708
606/86 A

FOREIGN PATENT DOCUMENTS

| EP | 316371 | 10/1991 |
| EP | 528177 | 2/1993 |
| EP | 1590077 | 5/2010 |
| WO | 9002527 | 3/1990 |
| WO | 2004014231 | 2/2004 |
| WO | 2005107415 | 11/2005 |
| WO | 2006094754 | 9/2006 |
| WO | 2006118998 | 11/2006 |
| WO | 2007092797 | 8/2007 |
| WO | 2008155772 | 12/2008 |

\* cited by examiner

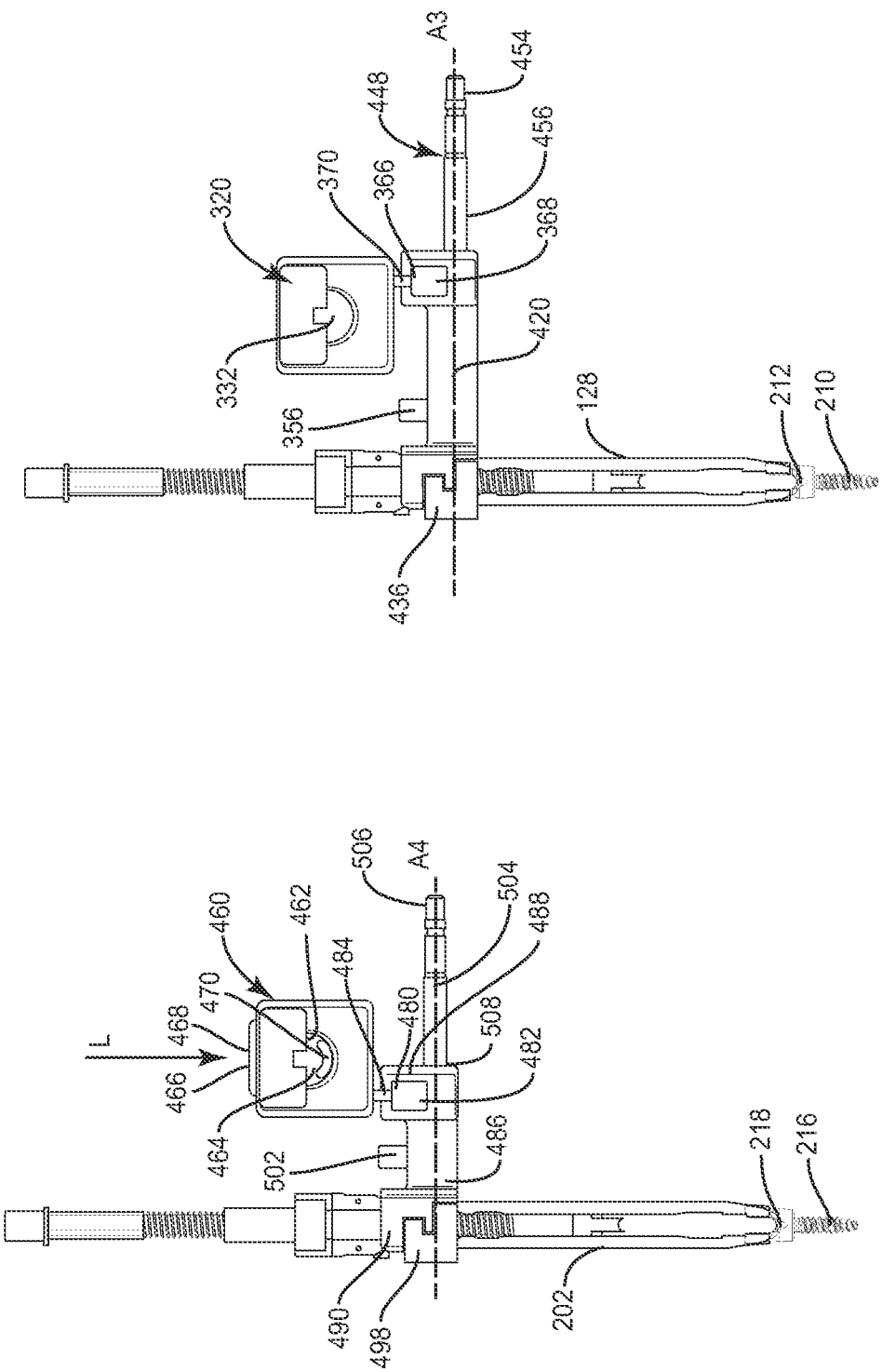

SURGICAL INSTRUMENT AND METHOD

TECHNICAL FIELD

The present disclosure generally relates to medical devices for the treatment of spinal disorders, and more particularly to a surgical instrument and method for correction of a spine disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, laminectomy, fusion and implantable prosthetics. Correction treatments used for positioning and alignment of vertebrae may employ implants, such as, for example, spinal constructs and interbody devices, for stabilization of a treated section of a spine. In some embodiments, the spinal constructs may be manipulated with surgical instruments for compression and distraction of vertebrae. This disclosure describes an improvement over these prior art technologies.

SUMMARY

In one embodiment, a surgical instrument is provided. The surgical instrument comprises a first member defining a longitudinal axis. A second member is disposed with the first member and is axially translatable relative to the first member. A first body is connected to the first member and is translatable along an arcuate path relative to the first member. The first body is connected to a first implant support. A second body is connected to the second member and is translatable along an arcuate path relative to the second member. The second body is connected to a second implant support. In some embodiments, systems and methods are disclosed.

BRIEF DESCRIPTION OF THE DRAWINGS

The present disclosure will become more readily apparent from the specific description accompanied by the following drawings, in which:

FIG. 17 is a side view of components of the system shown in FIG. 13;

FIG. 18 is a side view of components of the system shown in FIG. 13; and

DETAILED DESCRIPTION

Figure 1:
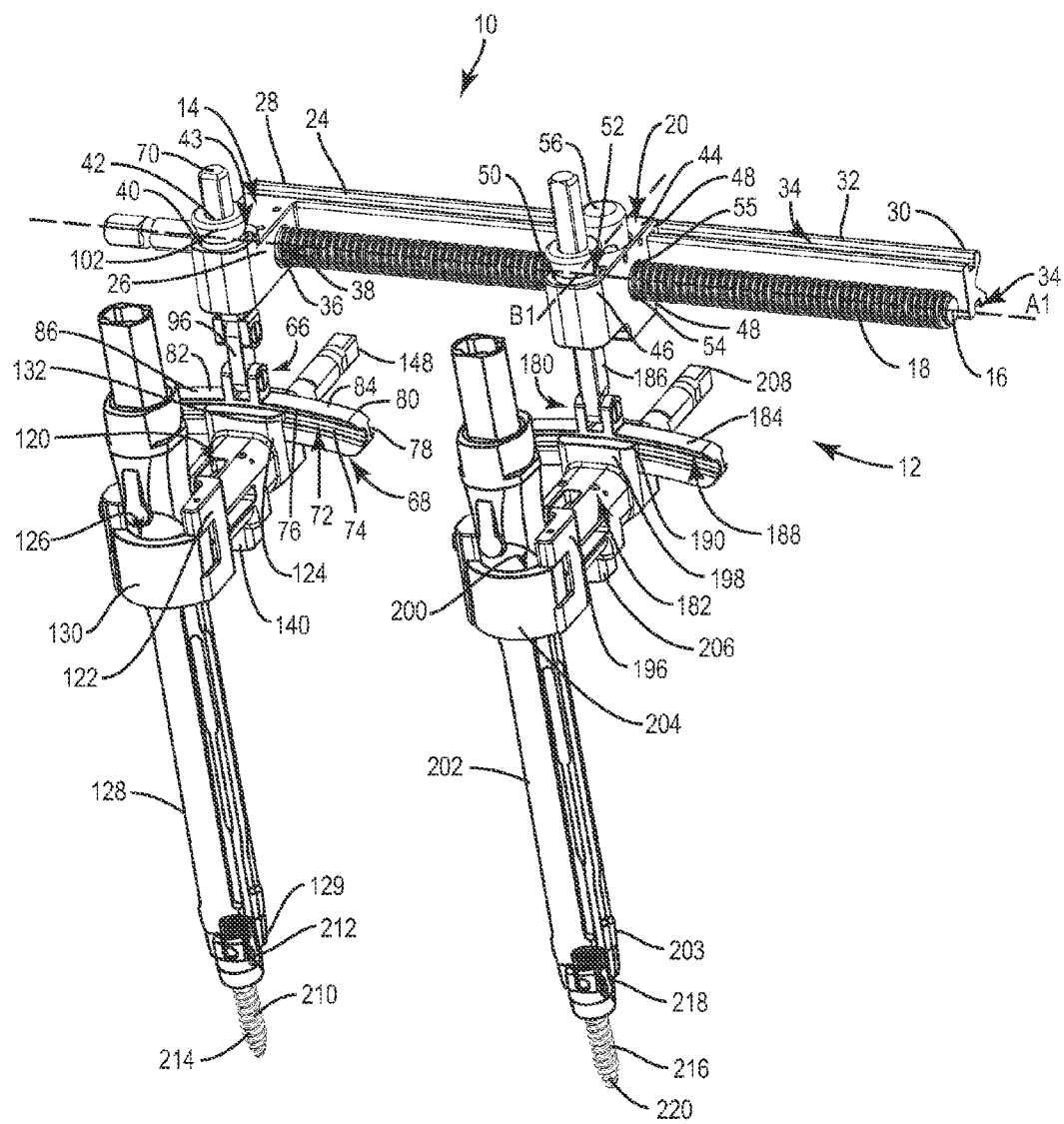
FIG. 1 is a perspective view of components one embodiment of a spinal correction system in accordance with the principles of the present disclosure.
Figure 2:
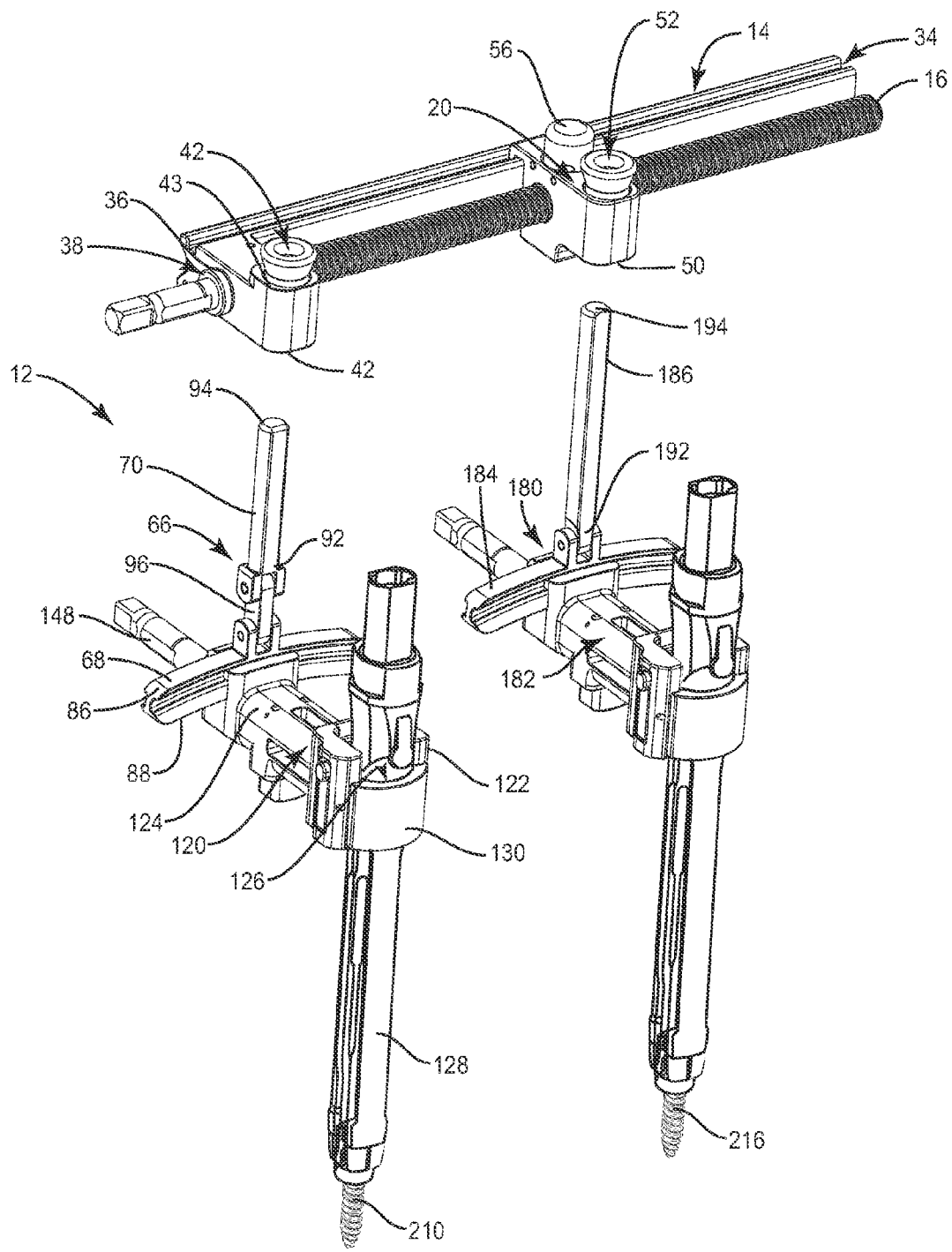
FIG. 2 is a perspective view of components of the system shown in FIG. 1 with parts separated.
Figure 3:
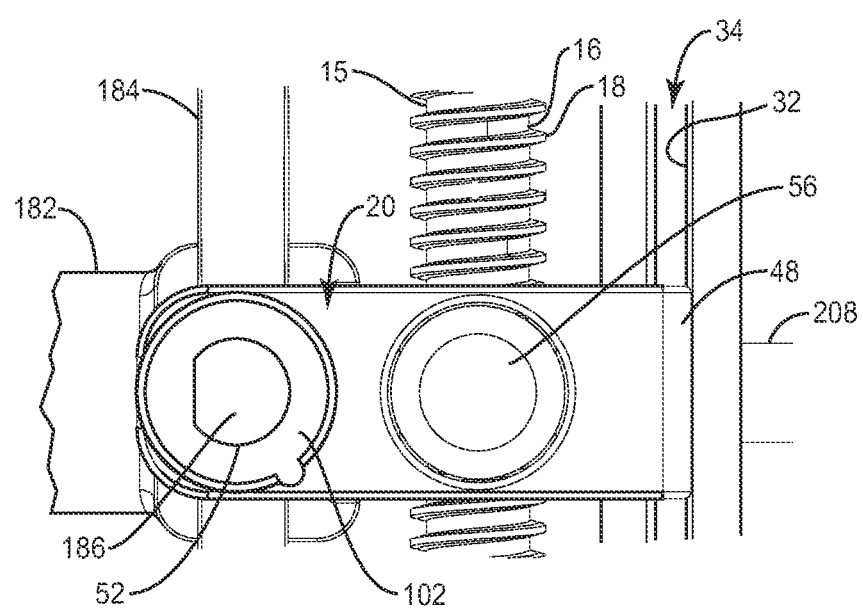
FIG. 3 is a breakaway view of components of the system shown in FIG. 1.

The exemplary embodiments of the system and related methods of use disclosed are discussed in terms of medical devices for the treatment of musculoskeletal disorders and more particularly, in terms of a surgical system and method for correction of a spine disorder.

In one embodiment, the system includes a surgical instrument that can compress or distract and restore curvature of a spine. In one embodiment, the surgical instrument is used to restore vertebral body height and lordosis after a trauma, such as, for example, a fall or car accident. In one embodiment, the system includes a surgical instrument, such as, for example, a thoracic compressor and distractor that can attach to implant supports, such as, for example, screw extenders via clips. The thoracic compressor and distractor includes a compression/distraction rack and a lordosis rack to control movement. In one embodiment, the compression or distraction is controlled via turning a threaded hex nut along the threaded compression/distraction rack. In one embodiment, a first box attached to the compression/distraction rack remains stationary relative to the compression/distraction rack while a second box with the hex nut attached to the compression/distraction rack compresses or distracts the extenders.

In one embodiment, lordosis racks are attached to the first and second compression/distraction boxes. In one embodiment, lordosis is controlled by rotating a pinion gear engaged to a geared surface of the lordosis racks. In one embodiment, the lordosis racks have an arc with a radius such that the center of rotation of the thoracic compressor and distractor corresponds to the radius. In some embodiments, the radius may correspond to the surgical instrument, an implant support, a bone screw and/or adjacent a portion of a patient's body, such as, for example, a facet joint. In one embodiment, locks are provided to lock the gears in place. In one embodiment, the center of rotation is below the skin near the facet joints. In one embodiment, the lordosis racks are positionable between a locked configuration and an unlocked configuration. In the unlocked configuration, a gear shaft can be axially translated between a first position and a second position. In the first position, the lordosis rack can be moved via turning the gear shaft. In the second position, the lordosis rack is freely movable. In one embodiment, to create parallel distraction, a handle is rotated causing a threaded rod of the compressions/distraction rack to rotate such that one of the compressor/distractor boxes translates along the threaded rod. In one embodiment, the extender clip includes a boss that is configured for disposal with an opening in an extender. In one embodiment, the clip includes a push button to release the clip.

In one embodiment, the lordosis racks are attached to the compressor/distractor rack via a hinge that is adjustable to align the thoracic compressor and distractor in a sagittal plane of a body, such as, for example, vertebrae. In one embodiment, the hinge includes one to two links. In one embodiment, each lordosis rack includes gear teeth on a bottom surface of its arc that are engageable with the gear shaft. In one embodiment, the gear shaft is disposed in a lordosis gear box. In one embodiment, to create lordosis, the gear shaft is pushed into the lordosis gear box and rotated such that the gear teeth rotate around the lordosis rack. In one embodiment, a hex is provided to lock the gear shaft in place relative to the lordosis gear box. In one embodiment, a pocket is provided in the lordosis gear box such that the gear shaft is movable into a position disengaged from the gear teeth of the lordosis rack. In one embodiment, grooves are provided in the lordosis gear box to retain the gear shaft. In one embodiment, retaining pins are provided in the lordosis gear box to resist movement of the gear shaft. In a free position, the gear shaft is in the pocket and the lordosis rack can move freely through the lordosis gear box. In a functional position, the gear shaft is constrained by the hex and pushing the gear shaft into the gear box will allow the gear shaft to rotate. In one embodiment, the lordosis rack includes slots that engage with a protrusion in the lordosis gear box to contain and guide the lordosis rack along the lordosis gear box.

In one embodiment, the lordosis racks each include a post extending substantially perpendicularly therefrom that are engageable with respective compressor/distractor boxes. In one embodiment, the posts are engageable with the compressor/distractor boxes via a locking mechanism. The locking mechanism includes ball bearings resiliently biased such that the ball bearings protrude from the post. In one embodiment, the locking mechanism includes a tapered inner passageway and a knob portion disposed with the compressor/distractor boxes and in the inner passageway. In one embodiment, the post is inserted into the knob and the ball bearings prevent the post from disengaging unless the knob is pulled upwards. In one embodiment, the post is free to move up and not down unless the knob is pulled upwards. In one embodiment, the post is shaped such that rotation relative to the knob is resisted and/or prevented.

In one embodiment, to assemble the surgical instrument, the gear shaft is placed in the free position and the lordosis rack is adjusted such that the post extends substantially perpendicular from the arcuate rack. The extender is attached to the instrument via the clips. A push release button is pressed and the knobs are positioned over the posts. The rack is pushed down over the posts as far as possible. Prior to spinal correction, the gear shafts are positioned in their functional positions. In one embodiment, lordosis correction and parallel distraction are independent of one another.

In some embodiments, one or all of the components of the system may be disposable, peel pack and/or pre packed sterile devices. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, vessels, ligaments, tendons, cartilage and/or bone unless specifically referred to otherwise.

The following discussion includes a description of a system in accordance with the principles of the present disclosure. Alternate embodiments are also disclosed. Reference is made in detail to the exemplary embodiments of the present disclosure, which are illustrated in the accompanying figures. Turning to FIGS. 1-12, there are illustrated components of a system, such as, for example, a spinal correction system 10 in accordance with the principles of the present disclosure.

The components of system 10 can be fabricated from biologically acceptable materials suitable for medical applications, including metals, synthetic polymers, ceramics, bone material, tissue and/or their composites, depending on the particular application and/or preference of a medical practitioner. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 includes a surgical instrument 12 configured for engagement with spinal constructs to correct a spinal disorder, such as, for example, trauma and/or fracture of vertebrae, which may include a sagittal deformity, as described herein. Instrument 12 includes a member, such as, for example, a compression-distraction rack 14. Rack 14 includes a linear shaft 16 defining a longitudinal axis A1. Shaft 16 has a cylindrical cross section configuration and an outer surface 18 having an external thread form threadably engageable with a member 20, as described herein. In some embodiments, the external thread form may include a single thread turn or a plurality of discrete threads. In some embodiments, shaft 16 has a variously configured cross section configuration, such as, for example, oval, oblong, triangular, rectangular, square, polygonal, irregular, uniform, non-uniform, variable and/or tapered.

Rack 14 includes an elongate member 24 and a flange 26. Elongate member 24 is spaced from shaft 16 and extends between an end 28 and an end 30 in a substantially parallel orientation relative to shaft 16. Elongate member 24 includes an inner surface 32 defining a linear cavity 34 extending along a length of elongate member 24 and on opposing sides of elongate member 24. Cavity 34 is configured for disposal of member 20, as described herein.

Flange 26 extends transversely from end 28 of elongate member 24 and includes an inner surface 36 defining a passageway 38 configured for disposal of shaft 16. Inner surface 36 has a smooth and cylindrical configuration such that shaft 16 is rotatable within passageway 38. In some embodiments, inner surface 36 is variously configured, such as, for example, rough, threaded for connection with surgical instruments, arcuate, undulating, dimpled, polished and/or textured. Flange 26 includes an inner surface 40 defining an inner passageway 43 extending transversely to inner passageway 38. Inner passageway 43 is configured for disposal of a coupling member 66, as described herein. Inner passageway 43 has a tapered configuration including a tapered section 98 and a uniform section 101 such that a post 70 is disposable in a friction fit engagement with tapered section 98, as described herein. Inner passageway 43 includes a capture member, such as, for example, a ring 100 extending into uniform section 101. Tapered section 98 includes a bearing configuration including ball bearings 112 to resist and/or prevent translation of post 70 in a first direction relative to rack 14, as described herein.

Instrument 12 includes member 20. Member 20 is disposed with rack 14 and is axially translatable along shaft 16 relative to rack 14. Member 20 extends between an end 44 and an end 46 defining a longitudinal axis B1 transverse to axis A1. End 44 includes a hook element 48, extending therefrom and engageable with cavity 34 such that hook element 48 is translatable through cavity 34 of elongate member 24. End 46 includes an inner surface 50 defining an inner passageway 52 configured for disposal of a coupling member 180, as described herein. Member 20 includes an inner threaded surface 54 engageable with outer surface 18 of shaft 16 such that as shaft 16 rotates, member 20 translates along axis A1. Inner threaded surface 54 defines an inner passageway 55 configured for disposal of shaft 16 and extending transverse to inner passageway 52.

Figure 4:
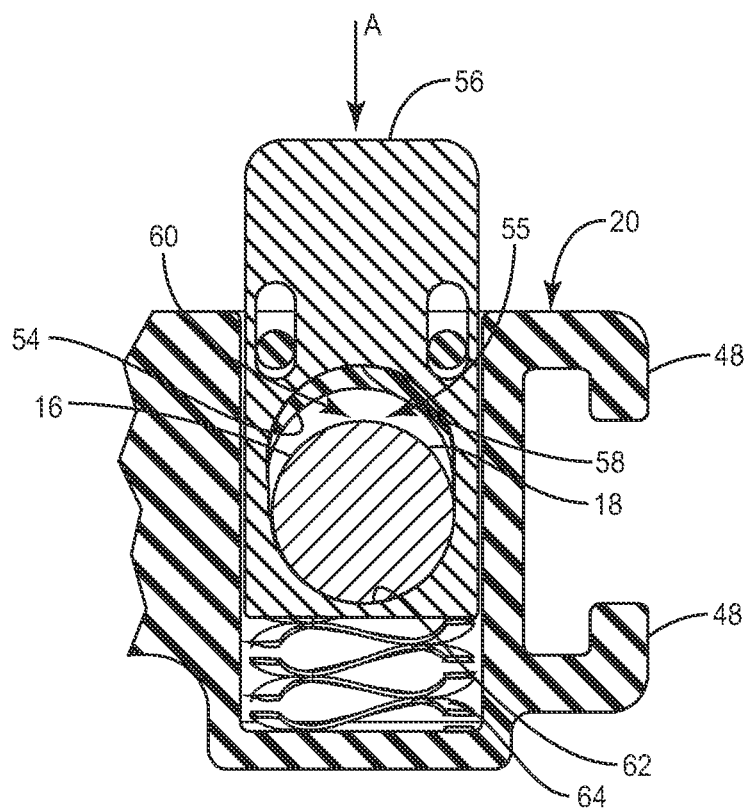
FIG. 4 is a breakaway view, in cross section, of components of the system shown in FIG. 1.

Member 20 includes a lock 56 that resists axial translation of member 20 relative to rack 14. Lock 56 is configured to selectively fix member 20 relative to rack 14. Lock 56 includes an inner surface 58 defining an opening 60 configured for disposal of shaft 16, as shown in FIG. 4. A lower portion 62 of inner surface 58 has an external thread form. In a locking orientation, lower portion 62 is threadably engaged with outer surface 18 of shaft 16 such that rotation of shaft 16 axially translates member 20 along shaft 16. Opening 60 has a circumference greater than a circumference of the cross section of shaft 16 such that in a non-locking orientation, shaft 16 is translatable through opening 60. Lock 56 is resiliently biased to the locking orientation via a biasing member, such as, for example, a spring 64. To orient lock 56 in the non-locking orientation, lock 56 is translated, in the direction shown by arrow A in FIG. 4, to overcome the resilient bias of spring 64, disengaging lower portion 62 from outer surface 18 of shaft 16 such that shaft 16 is translatable through opening 60 and inner passageway 55 without rotating shaft 16.

Figure 5:
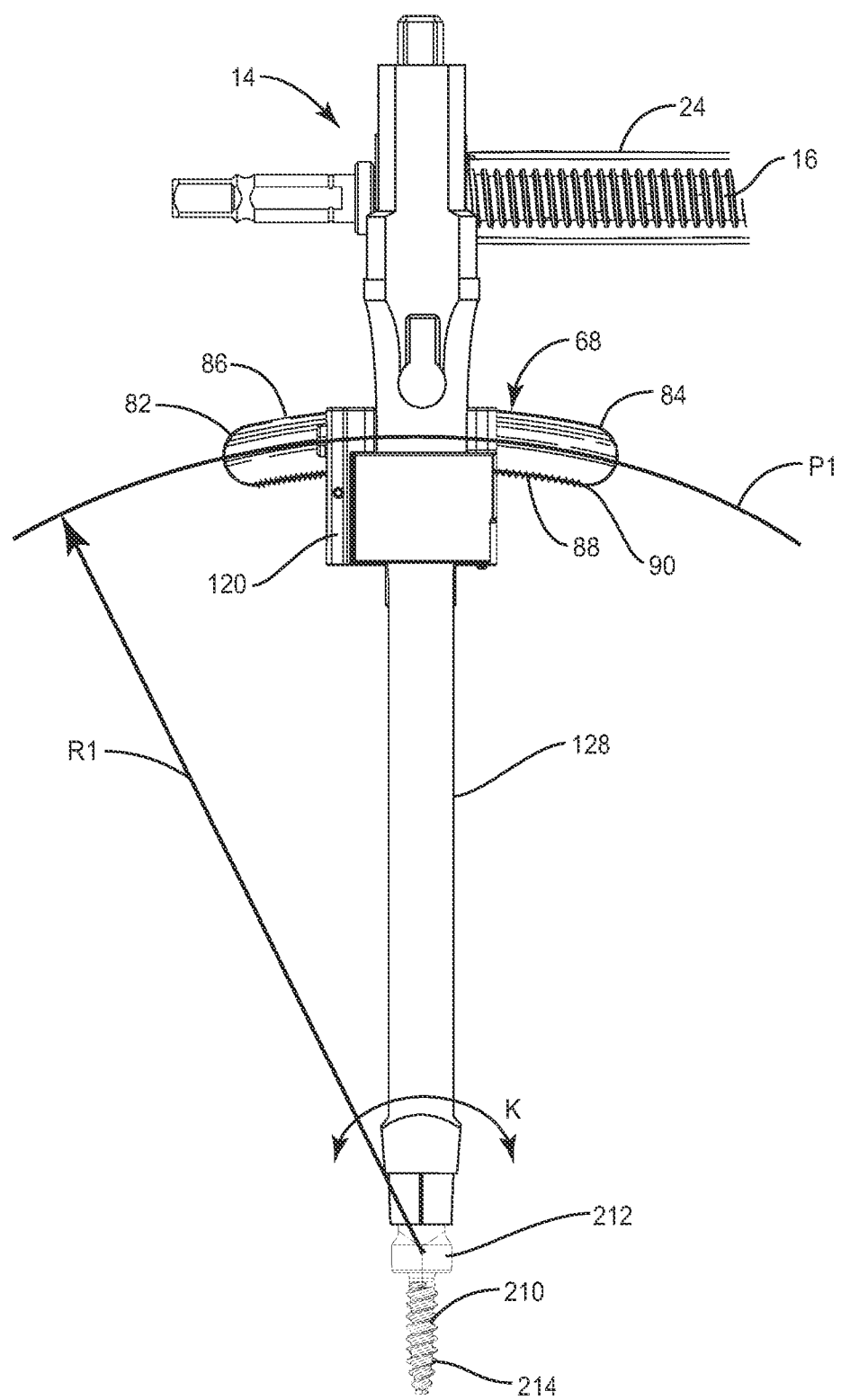
FIG. 5 is a breakaway plan view of components of the system shown in FIG. 1.

Instrument 12 includes coupling member 66. Coupling member 66 is disposed with rack 14 and a body 120, as described herein. Coupling member 66 includes a first portion, such as, for example, a gear rack 68 and a second portion, such as, for example, post 70. Gear rack 68 is disposable with rack 14. Gear rack 68 has an arcuate configuration having a radius of curvature R1 defining an arcuate path P1, as shown in FIG. 5. Gear rack 68 is disposed with rack 14 and body 120 such that body 120 is translatable along arcuate path P1, as described herein. In some embodiments, gear rack 68 is variously configured, such as, for example, round, oval, oblong, irregular, uniform, non-uniform, consistent, variable, horseshoe shape, U-shape or kidney bean shape.

Gear rack 68 includes a male mating part 72 configured for mating engagement with an inner surface of a female mating part 132 of body 120, as described herein. Male mating part 72 defines a cavity 74 disposed on a lateral side 76 of gear rack 68 and a cavity 78 disposed on a lateral side 80 of gear rack 68. Cavities 74, 78 extend between an end 82 and an end 84 of gear rack 68 such that body 120 is translatable between ends 82, 84 of gear rack 68. Gear rack 68 includes an upper surface 86 connected to post 70 and a bottom outer surface, such as, for example, a toothed outer surface 88, as shown in FIG. 5. Surface 88 includes a series of teeth 90 engageable with a rotatable shaft 148 of body 120, as described herein, such that the rotation of shaft 148 translates body 120 along arcuate path P1 relative to gear rack 68 and rack 14.

Post 70 extends between an end 92 and an end 94. End 92 is connected to upper surface 86 of gear rack 68 via a hinge 96. Hinge 96 includes a first link and a second link such that post 70 and gear rack 68 are positionable in a plurality of orientations relative to one another. In some embodiments, hinge 96 includes one link. In some embodiments, hinge 96 may be variously configured such as, for example, pin, post, screw, living hinge, ratchet and/or concentric parts. In some embodiments, gear rack 68 is integrally connected to or monolithically formed with post 70 such that post 70 extends in a substantially perpendicular orientation from gear rack 68. Post 70 has a non-uniform cylindrical cross section configuration, such as, for example, a D-shaped cross section configuration such that rotation of post 70 relative to rack 14 is resisted and/or prevented. In some embodiments, post 70 may have various cross section configurations, such as, for example, oval, oblong, triangular, rectangular, square, polygonal, irregular, uniform, non-uniform, variable and/or tapered.

End 94 of post 70 is disposable in an inner passageway 42, defined within a knob portion 102 of rack 14, between a locking configuration and a non-locking configuration, as described herein. Post 70 is translatable along inner passageway 42 in the first direction, as shown by arrow B in FIGS. 6 and 7, and a second, opposing direction, as shown by arrow C. Post 70 includes knob portion 102, which is disposable about post 70 and translatable relative to post 70, in the directions shown by arrows B and C. Knob portion 102 extends between an end 104 having a handle 108 and an end 106 having a radially extending flange 110. A biasing member, such as, for example, a spring 114 is disposed between handle 108 and flange 110.

Figure 6:
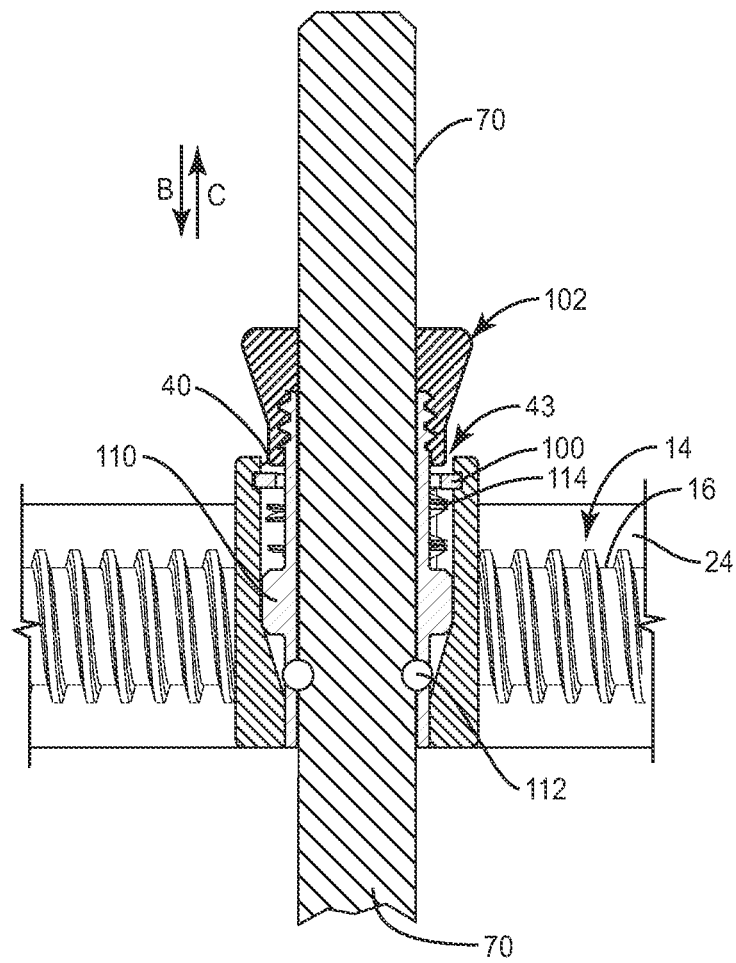
FIG. 6 is a breakaway view, in part cross section, of components of the system shown in FIG. 1.
Figure 7:
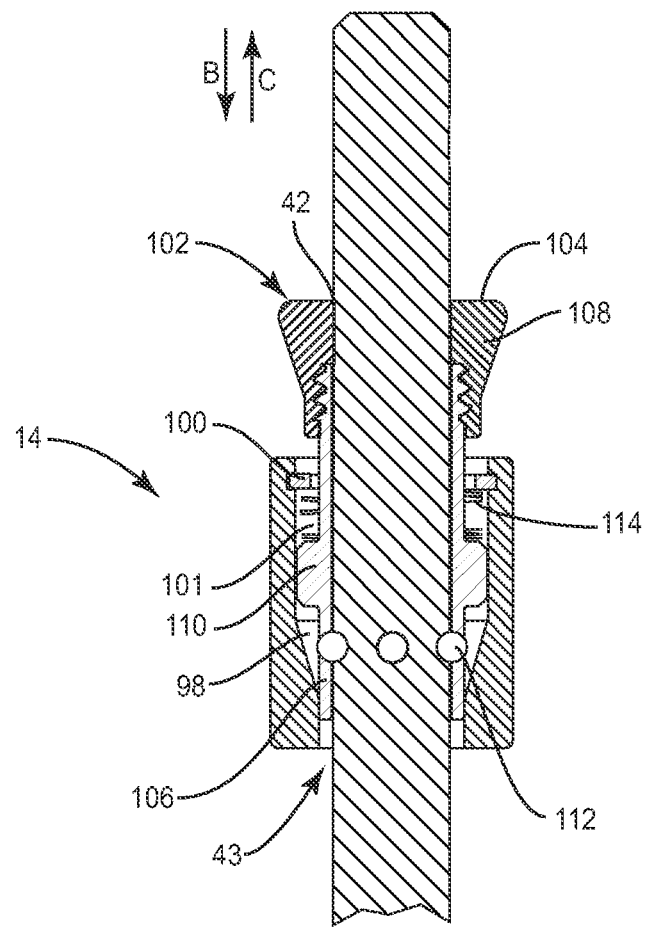
FIG. 7 is a side view, in cross section, of components of the system shown in FIG. 6.

In the locking configuration, as shown in FIG. 6, knob portion 102 is disposed in inner passageway 43 such that spring 114 is captured between ring 100 and flange 110 to bias ball bearings 112 towards tapered section 98 of inner passageway 43. Ball bearings 112 are disposed in tapered section 98 and in frictional engagement with post 70 such that movement of rack 14 relative to post 70, in the direction shown by arrow C, is resisted and/or prevented. To transition between the locking configuration to the non-locking configuration, a force is applied to handle 108, in the direction shown by arrow C, to translate knob portion 102 relative to post 70 such that ball bearings 112 are moved out of frictional engagement with post 70. In the non-locking configuration, rack 14 is translatable with knob portion 102, in the direction shown by arrow C, relative to post 70 and/or post 70 is translatable, in the direction shown by arrow B, relative to knob portion 102 and rack 14.

Instrument 12 includes body 120. Body 120 is connected to rack 14 via coupling member 66. Body 120 is translatable along arcuate path P1 relative to gear rack 68 to rotate an extender 128 attached to a fastener 210. Body 120 translates along path P1 and rotates about a center of rotation, such as, for example, from a radius R1, which corresponds to a portion of fastener, such as, for example, the connection of head 212 and shaft 214. As such, translation of body 120 along path P1 rotates fastener 210, in the directions shown by arrows K in FIG. 5, to rotate vertebra to achieve lordosis and restore curvature of a spine during treatment of a disorder such as trauma, which may include correction of a sagittal deformity, as described herein.

Body 120 extends between an end 122 and an end 124. End 122 defines a cavity 126 configured for disposal of an implant support, such as, for example, extender 128 disposed with a vertebral body V1, as described herein. In some embodiments, the implant support can include alternate instruments, such as, for example, drivers, reducers, extended tab screws, inserters, spreaders, distractors, blades, clamps, forceps, elevators and drills. In some embodiments, body 120 is monolithically formed with the implant support such that body 120 is directly connected to a bone screw disposed with vertebral body V1. End 122 includes a capture element, such as, for example, a clip 130 to engage extender 128. Clip 130 has a C-shape configuration. In some embodiments, clip 130 is variously configured, such as, for example, round, oval, oblong, triangular, polygonal having planar or arcuate side portions, irregular, uniform, non-uniform, consistent, variable, horseshoe shape, U-shape or kidney bean shape. Clip 130 is releasably engageable with end 122. In the engaged position, clip 130 encloses extender 128 to capture extender 128 in cavity 126.

Figure 9:
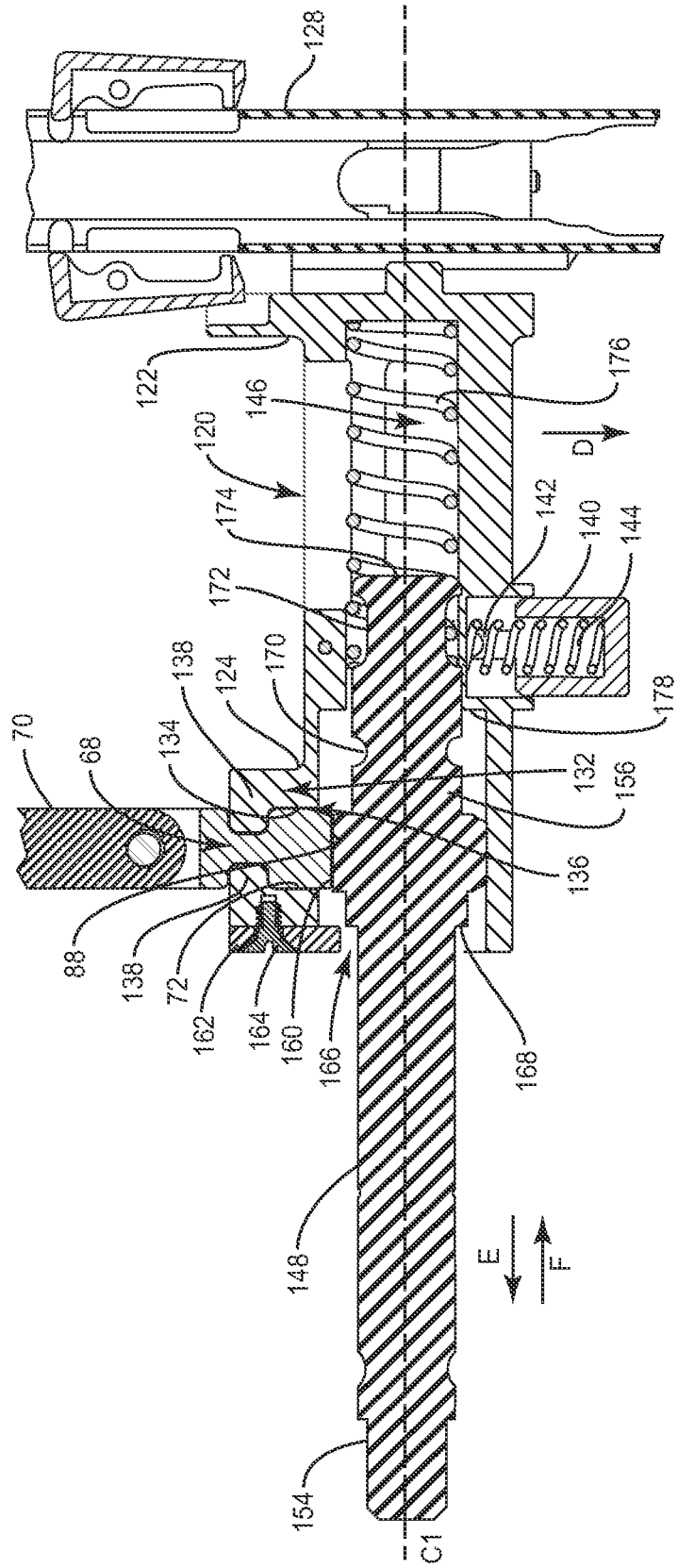
FIG. 9 is a breakaway view, in cross section, of components of the system shown in FIG. 1.
Figure 10:
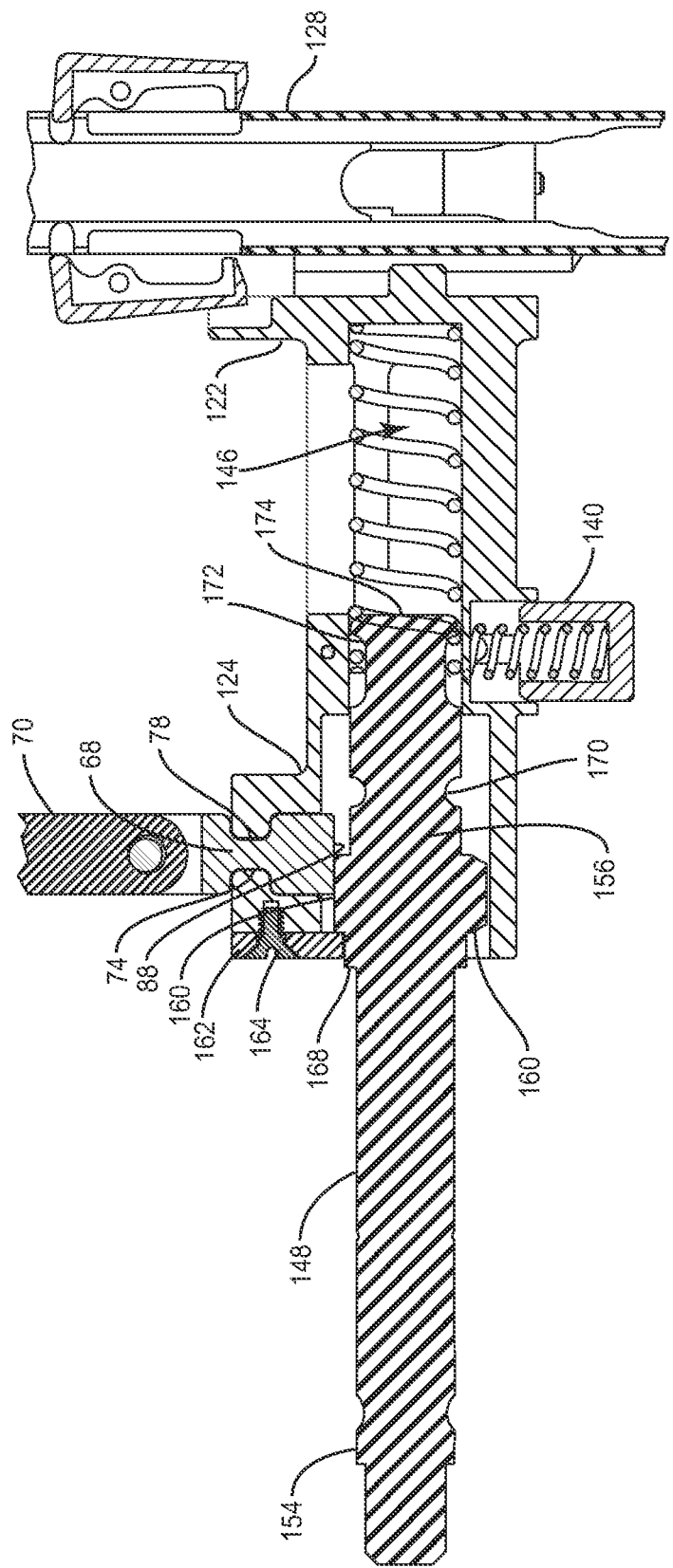
FIG. 10 is a breakaway view, in cross section, of components of the system shown in FIG. 1.
Figure 11:
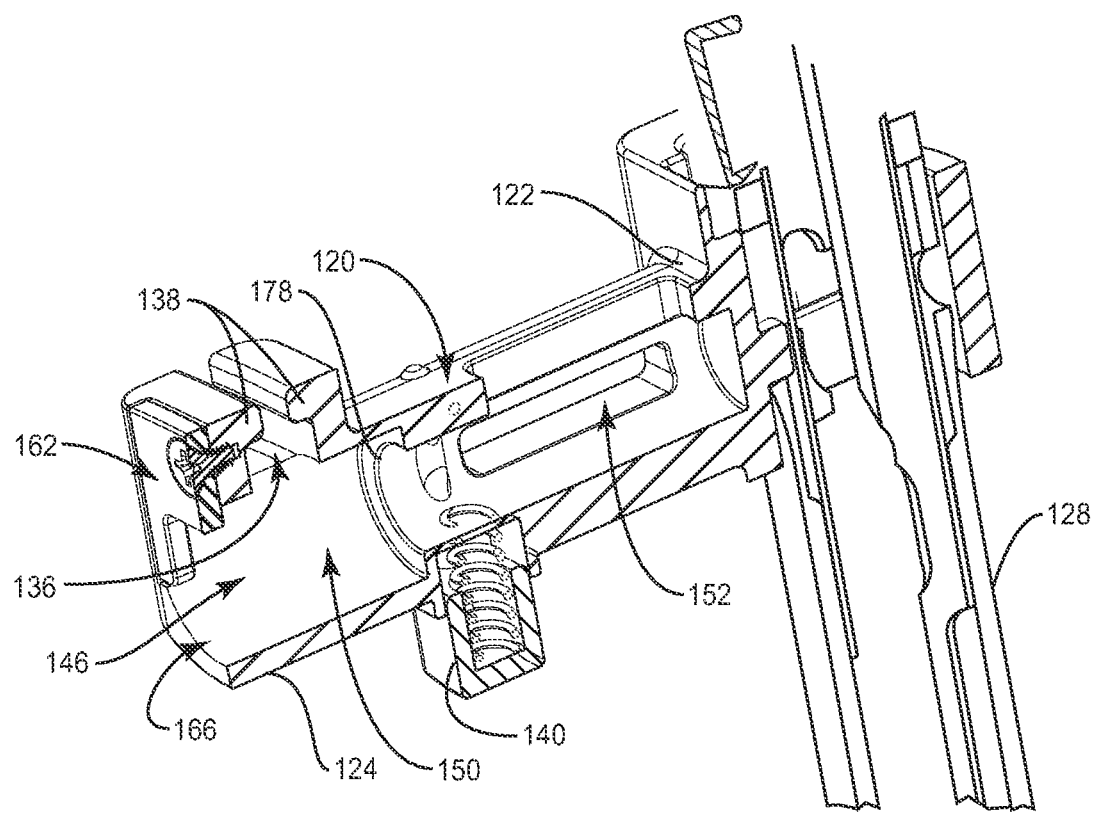
FIG. 11 is a cutaway view of the components shown in FIG. 10.

End 124 of body 120 includes female mating part 132 having an inner surface 134 defining a passageway 136 configured for mating engagement with male mating part 72 of gear rack 68, as shown in FIGS. 9-11. Female mating part 132 includes opposing flanges 138 configured for mating engagement with cavities 74, 78 on lateral sides 76, 80 of gear rack 68.

Body 120 includes a lock 140 disposed between ends 122, 124 of body 120 and configured to selectively fix body 120 relative to gear rack 68. Lock 140 includes a pin 142 and a biasing member, such as, for example, a spring 144 resiliently biasing pin 142 towards a cavity 146 of body 120. Body 120 defines cavity 146 between ends 122, 124. Cavity 146 is configured for disposal of rotatable shaft 148, as described herein. Cavity 146 includes a section 150 and a section 152, narrower in circumference than section 150, as shown in FIG. 11.

Body 120 includes rotatable shaft 148. Shaft 148 is translatable within cavity 146 between a first position, such as, for example, a first non-locking orientation, as shown in FIGS.

Figure 8:
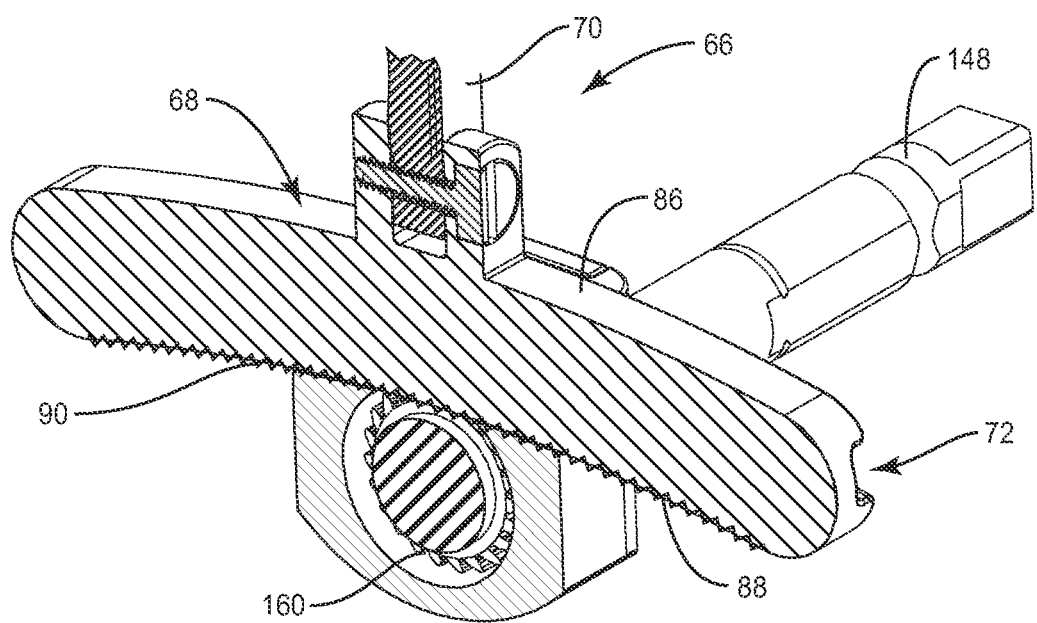
FIG. 8 is a breakaway view of components of the system shown in FIG. 1.
Figure 12:
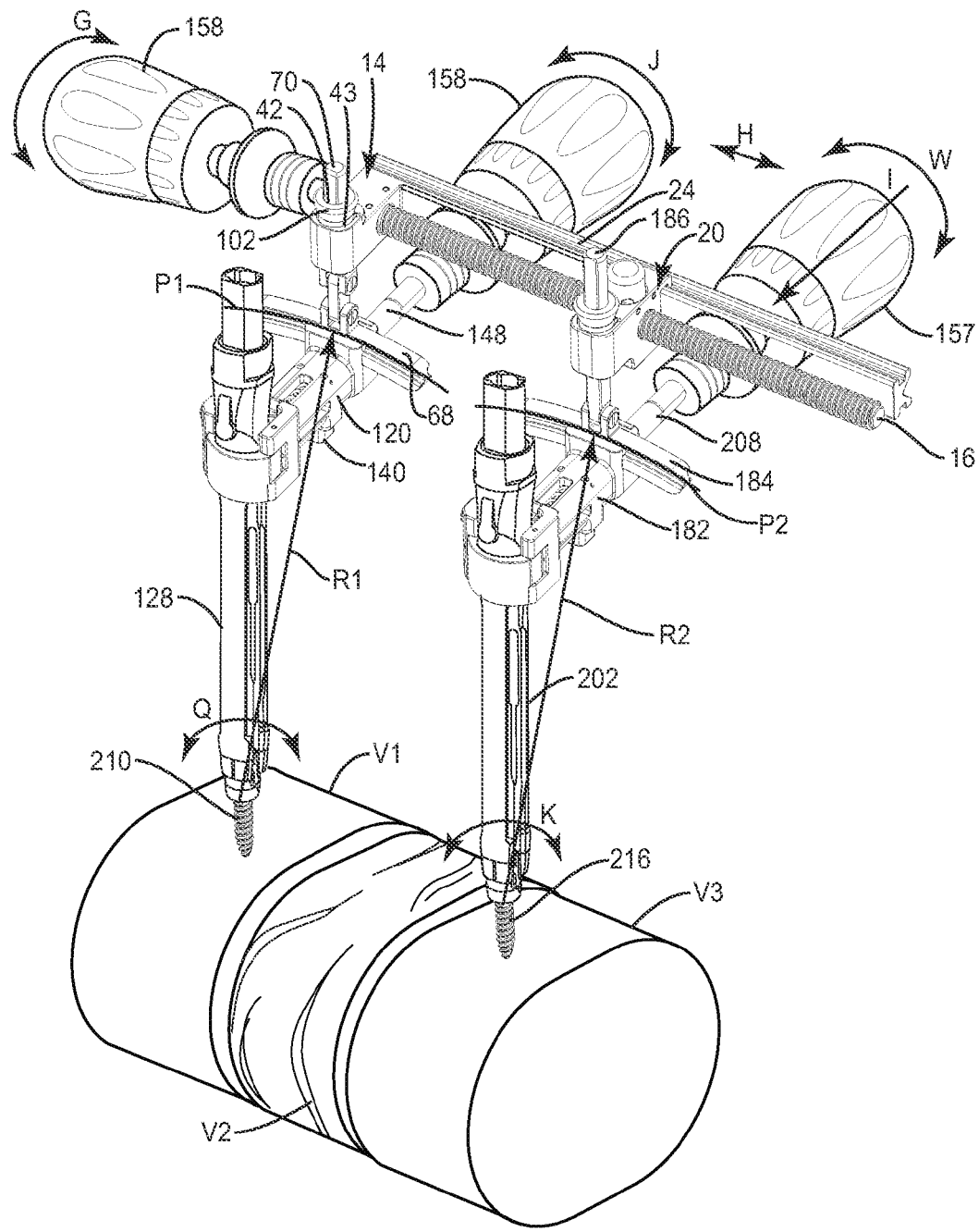
FIG. 12 is a perspective view of components of one embodiment of a spinal correction system in accordance with the principles of the present disclosure, disposed with vertebrae.

8-9, a second position, such as, for example, a second non-locking orientation (not shown) and a third position, such as, for example, a locking orientation, as shown in FIG. 10, as described herein. Shaft 148 extends between an end 154 and an end 156. End 154 is configured for releasable engagement with a handle 158, as shown in FIG. 12, to actuate the rotation of shaft 148. In some embodiments, handle 158 includes an outer gripping surface configured for gripping by a hand of a practitioner. In some embodiments, the gripping surface may be, such as, for example, those alternatives described herein. End 156 includes a gear portion 160 connected with gear rack 68 in the locking orientation and the first non-locking orientation. Gear portion 160 protrudes radially from shaft 148 and is configured for engagement with toothed outer surface 88 of gear rack 68 in the first non-locking orientation, as shown in FIGS. 8-9, to translate body 120 in arcuate path P1 along gear rack 68 and relative to rack 14.

A plate 162 connects with end 124 of body 120 via a screw, post and/or pins 164 to capture shaft 148 in cavity 146. End 124 and plate 162 together define an opening 166 having a hexagonal cross section configuration. Shaft 148 includes a radial extension 168 configured for disposal in opening 166 of body 120 in the locking orientation, as shown in FIG. 10. Extension 168 has a hexagonal cross section configuration corresponding to the cross section configuration of opening 166 such that extension 168 resists and/or prevents rotation of shaft 148 within cavity 146. In the locking orientation, as shown in FIG. 10, extension 168 is disposed in opening 166 such that rotation of shaft 148 is resisted and/or prevented and a portion of gear portion 160 is engaged with toothed outer surface 88 of gear rack 68 such that gear portion 160 resists and/or prevents the translation of gear rack 68 relative to body 120. In some embodiments, opening 166 and extension 168 have various cross section configurations, such as, for example, those alternatives described herein, to resist and/or prevent rotation of extension 168 within opening 166.

Shaft 148 includes an annular groove 170 disposed adjacent gear portion 160. Groove 170 has a circular configuration. Groove 170 is configured for disposal of pin 142 in the second non-locking orientation (not shown) such that pin 142 resists and/or prevents the axial translation of shaft 148. To move shaft 148 from the locking orientation to one of the non-locking orientations, pin 142 is axially translated, in a direction shown by arrow D in FIG. 9, such that shaft 148 is translatable, in the direction shown by arrow E in FIG. 9, along longitudinal axis C1. Shaft 148 includes an annular groove 172 disposed between groove 170 and a distal tip 174 of shaft 148. Groove 170 has an elongated configuration. Groove 172 is configured for disposal of pin 142 in the locking orientation and the first non-locking orientation such that pin 142 resists and/or prevents movement of shaft 148 from the first non-locking orientation to the second non-locking orientation. In some embodiments, grooves 170, 172 are variously configured, such as, for example, circular, oval, oblong, triangular, rectangular, polygonal, irregular, uniform, non-uniform, offset, staggered, variable, U-shape and/or kidney bean shape.

Body 120 includes a biasing member, such as, for example, a spring 176 disposed in section 152 of cavity 146 between end 122 of body 120 and distal tip 174 of shaft 148 to resiliently bias shaft 148 to the locking orientation, as shown in FIG. 10. A lip 178 extending into section 150 of cavity 146 resists the axial translation of gear portion 160 from section 150 into section 152 of cavity 146. To move shaft 148 from the locking orientation to the first non-locking orientation, shaft 148 is axially translated, in a direction shown by arrow F in FIG. 9, to overcome the resilient bias of spring 176. In the first non-locking orientation, gear portion 160 is engaged to toothed outer surface 88 of gear rack 68 and extension 168 is disengaged from plate 162. To move shaft 148 from the locking orientation or the first non-locking orientation to the second non-locking orientation (not shown), shaft 148 is translated in cavity 146, in the direction shown by arrow F, such that gear portion 160 is disposed adjacent lip 178 in section 150 of cavity 146. In the second non-locking orientation, gear portion 160 is disengaged from gear rack 68 such that body 120 is translatable along arcuate path P1 through cavity 146 without rotating shaft 148.

Instrument 12 includes a coupling member 180, similar to coupling member 66 described herein, disposed with member 20 and a body 182, as described herein. Coupling member 180 includes a portion, such as, for example, a gear rack 184, similar to gear rack 68 described herein, and a portion, such as, for example, a post 186, similar to post 70. Gear rack 184 is disposable with member 20. Gear rack 184 has an arcuate configuration having a radius of curvature R2 defining an arcuate path P2. Gear rack 184 is disposed with member 20 and body 182 such that body 182 is translatable along arcuate path P2. Gear rack 184 includes a male mating part 188, similar to mating part 72 described herein, configured for mating engagement with a female mating part 190, similar to mating part 132 described herein, of body 182. Post 186 extends between an end 192 and an end 194. End 192 is integrally connected to or monolithically formed with gear rack 184 such that post 186 is oriented substantially perpendicular to gear rack 184. In some embodiments, post 186 is connected to gear rack 184 via a hinge, similar to hinge 96. Post 186 is disposable in inner passageway 52 of member 20 between a locking and a non-locking configuration, similar to that described herein with regard to post 70.

Instrument 12 includes body 182. Body 182 is connected to member 20 via coupling member 180. Body 182 is translatable along arcuate path P2 along gear rack 184 and relative to member 20. Body 182 extends between an end 196 and an end 198. End 196 defines a cavity 200 configured for disposal of an implant support, such as, for example, an extender 202, similar to the implant supports described herein, disposed with a vertebral body V2, as described herein. End 196 includes a capture element, such as, for example, a clip 204, similar to clip 130 described herein, to capture extender 202 in cavity 200. Body 182 includes a lock 206, similar to lock 140 described herein, disposed between ends 196, 198 of body 182 and configured to selectively fix body 182 relative to gear rack 184. Body 182 defines a cavity (not shown) extending between ends 196, 198, similar to cavity 146 described herein, configured for disposal of a rotatable shaft 208, similar to shaft 148 described herein. The rotation of shaft 208 translates body 182 along arcuate path P2 relative to gear rack 184 and member 20 in a similar manner described herein with regard to shaft 148 and gear rack 68. In some embodiments, body 182 and the implant support can be monolithically formed to directly connect body 182 to a bone screw disposed with vertebral body V2, similar to that described herein.

System 10 includes a spinal construct, such as, for example, a bone fastener 210 engaged to a distal end 129 of extender 128 and configured for disposal with tissue, such as, for example, a vertebral body and rotation therewith. Bone fastener 210 includes a head 212 configured for attachment with extender 128, and an elongated shaft 214 configured for penetrating tissue. Shaft 214 has a cylindrical cross section configuration and includes an outer surface having an external thread form. In some embodiments, the thread form may include a single thread turn or a plurality of discrete threads.

In some embodiments, other engaging structures may be disposed on shaft 214, such as, for example, a nail configuration, barbs, expanding elements, raised elements and/or spikes to facilitate engagement of shaft 214 with tissue, such as, for example, vertebrae.

In some embodiments, all or only a portion of shaft 214 may have alternate cross section configurations, such as, for example, oval, oblong, triangular, square, polygonal, irregular, uniform, non-uniform, offset, staggered, undulating, arcuate, variable and/or tapered. In some embodiments, the outer surface may include one or a plurality of openings. In some embodiments, all or only a portion of the outer surface may have alternate surface configurations to enhance fixation with tissue such as, for example, rough, arcuate, undulating, mesh, porous, semi-porous, dimpled and/or textured. In some embodiments, all or only a portion of shaft 214 may be disposed at alternate orientations, relative to a longitudinal axis of bone fastener 210, such as, for example, transverse, perpendicular and/or other angular orientations such as acute or obtuse, co-axial and/or may be offset or staggered. In some embodiments, all or only a portion of shaft 214 may be cannulated.

In some embodiments, shaft 214 may be made for attachment to bone, such as cervical, thoracic, lumbar and or sacral vertebral bone structures, or other tissues. In one embodiment, shaft 214 may be a screw, or could also be alternatively configured, for example, as a vertebral hook or clamp. In some embodiments, the threads may be self-tapping or intermittent, or may have more than one crest winding about shaft 214. In one embodiment, the outer surface may include an opening for accommodating a tool (not shown) for gripping or turning bone fastener 210.

System 10 includes a spinal construct, such as, for example, a bone fastener 216, similar to bone fastener 210 described herein, engaged to a distal end 203 of extender 202 and configured for disposal with tissue, such as, for example, a vertebral body and rotation therewith. Bone fastener 216 includes a head 218 configured for fixation with extender 202 and an elongated shaft 220 configured for penetrating tissue.

In operation, to treat a condition of the spine, such as, for example, trauma of the spine, instrument 12 is manipulated for engagement with extenders 128, 202 such that fasteners 210, 216 are movable from a first configuration, which may include fasteners 210, 216 being disposed in an initial axial position and in an initial angle relative to one another and a second configuration, which may include fasteners 210, 216 being disposed at a corrected axial position and angle relative to one another. In some embodiments, instrument 12 is employed to treat vertebrae such that selected vertebra can be relatively translated for substantially axial compression or distraction to restore vertebral body height and rotated to achieve lordosis and restore curvature of the spine.

Instrument 12 is disposed adjacent a surgical site and manipulated for engagement with fasteners 210, 216 via extenders 128, 202 such that vertebrae can be axially distracted or compressed to treat trauma. Extenders 128, 202 are disposed in cavities 126, 200 of bodies 120, 182 and clips 130, 204 are engaged to ends 122, 196 of bodies 120, 182 to capture extenders 128, 202 in cavities 126, 200, respectively.

To position body 120 in a selected orientation relative to gear rack 68 prior to distraction or compression of vertebrae, lock 140 is translated, in the direction shown by arrow D in FIG. 9, to disengage pin 142 from groove 172 and shaft 148 is translated, in the direction shown by arrow F in FIG. 9, to the second non-locking orientation (not shown) so that body 120 can be translated along gear rack 68 without rotating shaft 148. With pin 142 disposed in groove 170, body 120 is translated along arcuate path P1 along gear rack 68 such that post 70 is in perpendicular alignment with shaft 148. Shaft 148 is moved from the second non-locking orientation to the first non-locking orientation so that body 120 can be translated along arcuate path P1 via rotation of shaft 148. Pin 142 is disengaged from groove 170 and shaft 148 is axially translated, in the direction shown by arrow E in FIG. 9, into the first non-locking orientation such that gear portion 160 is engaged with toothed outer surface 88 of gear rack 68 and pin 142 is disposed in groove 172. In the first non-locking orientation, body 120 can be translated along gear rack 68 along arcuate path P1 via rotating gear shaft 148. To position body 182 in a selected orientation relative to gear rack 184, a similar process is used as discussed with regard to body 120.

Members 14, 20 are aligned with posts 70, 186, to connect members 14, 20 with coupling members 66, 180. To align members 14, 20 with posts 70, 186, respectively, a force is applied to lock 56 to translate lock 56, in the direction shown by arrow A in FIG. 4, to disengage lower portion 62 from outer surface 18 of shaft 16. With lock 56 in the non-locking orientation, member 20 is axially translated along shaft 16 such that inner passageway 52 of member 20 is in coaxial alignment with post 186 of coupling member 180. With members 14, 20 in alignment with posts 70, 186, posts 70, 186 are inserted within inner passageways 42, 52 of members 14, 20 to connect members 14, 20 with coupling members 66, 180, respectively.

With members 14, 20 connected with coupling members 66, 180, instrument 12 can be disposed with vertebrae and used to axially translate vertebrae for compression or distraction of vertebrae. Prior to applying a linear distraction or compression force to vertebrae, shaft 208 is oriented in the locking orientation such that translation of member 20 along shaft 16 does not cause relative movement between body 182 and gear rack 184 such that member 20, coupling member 180, body 182, extender 202 and fastener 216 axially translate as one unit. With shaft 208 in the locking orientation, handle 158 is engaged to shaft 16 of rack 14 and rotated, in the directions shown by arrows G in FIG. 12, such that member 20 with coupling member 180, body 182, extender 202 and fastener 216 axially translate along shaft 16, in the directions shown by arrows H in FIG. 12, relative to rack 14, to apply a distraction or compression force to vertebrae.

A rotational force is applied to vertebrae to restore lordosis. To apply a rotational force to vertebrae, shaft 148 is oriented in the first non-locking orientation so that body 120 translates along gear rack 68 along arcuate path P1 as shaft 148 rotates, as described herein. Handle 158 is rotated, in the directions shown by arrows J in FIG. 12, such that body 120 translates along arcuate path P1 along gear rack 68 relative to member 14. Relative translation of body 120 along arcuate path P1 rotates fastener 210, which is connected to body 120 via extender 128, at a center of rotation from body 120 corresponding to radius R1. Fastener 210 rotates, as shown by arrows Q, to rotate vertebra V1 to achieve lordosis and restore curvature of vertebrae V to treat the fracture of vertebra V2. Shaft 208 is oriented in the first non-locking orientation so that body 182 translates along gear rack 184 along arcuate path P2 as shaft 208 rotates, as described herein.

Handle 157, similar to handle 158 described herein, is rotated, in the directions shown by arrows W in FIG. 12, such that body 182 translates along arcuate path P2 along gear rack 184 relative to member 20. Relative translation of body 182 along arcuate path P2 rotates fastener 216, which is connected to body 182 via extender 202, at a center of rotation from body 182 corresponding to radius R2. Fastener 216 rotates, as shown by arrows K, to rotate vertebra V3 to achieve lordosis and restore curvature of vertebrae V to treat the fracture of vertebra V2. In some embodiments, this configuration of instrument 12 compresses and/or distracts vertebra V to restore vertebral body height and restores curvature of vertebrae V by rotating vertebra about a center of rotation corresponding to a bone fastener adjacent a facet joint.

In assembly, operation and use, system 10, similar to that described above, is employed with a surgical procedure, such as, for example, a correction treatment to treat trauma of the spine, such as, for example, thoracolumbar and lumbar fractures. In some embodiments, one or all of the components of system 10 can be delivered or implanted as a pre-assembled device or can be assembled in situ. System 10 may be completely or partially revised, removed or replaced.

For example, system 10 can be employed with a surgical correction treatment of an applicable condition or injury, such as, for example, a trauma of an affected section of a spinal column and adjacent areas within a body, such as, for example, a fractured vertebra V2 of vertebrae V. In some embodiments, system 10 may be employed with one or a plurality of vertebra.

A medical practitioner obtains access to a surgical site including vertebrae V in any appropriate manner, such as through incision and retraction of tissues. Once access to the surgical site is obtained, the particular surgical procedure can be performed for treating a trauma, such as, for example, a spinal fracture.

An incision is made in the body of the patient and a cutting instrument (not shown) creates a surgical pathway for implantation of components of system 10. A preparation instrument (not shown) can be employed to prepare tissue surfaces of vertebrae V, as well as for aspiration and irrigation of a surgical region.

Pilot holes or the like are made in selected vertebra V1 and V3 of vertebrae V adjacent fractured vertebra V2 for receiving bone fasteners 210, 216, with fractured vertebra V2 being disposed between vertebrae V1, V3. A driver (not shown) is disposed adjacent vertebrae V at a surgical site and is manipulated to drive, torque, insert or otherwise connect bone fasteners 210, 216 adjacent vertebrae V1 and V3. Extenders 128, 202 are delivered to the surgical site adjacent vertebrae V and oriented for manipulation, alignment and capture of bone fasteners 210, 216. Extender 128 is connected to bone fastener 210 and extender 202 is connected to bone fastener 216.

Instrument 12 is engaged with extenders 128, 202 such that fasteners 210, 216 are movable from a first configuration, which may include fasteners 210, 216 being disposed in an initial axial position and in an initial angle relative to one another and a second configuration, which may include fasteners 210, 216 being disposed at a corrected axial position and angle relative to one another.

Instrument 12 is disposed adjacent a surgical site and manipulated for engagement with fasteners 210, 216 via extenders 128, 202. Extenders 128, 202 are disposed in cavities 126, 200 of bodies 120, 182 and clips 130, 204 are engaged to ends 122, 196 of bodies 120, 182 to capture extenders 128, 202 in cavities 126, 200, respectively.

Body 120 is disposed in a selected orientation relative to gear rack 68, and body 182 is disposed in a selected orientation relative to gear rack 184, as described herein. Members 14, 20 are aligned with posts 70, 186, to connect members 14, 20 with coupling members 66, 180, as described herein. Shaft 208 is oriented in the locking orientation such that translation of member 20 along shaft 16 does not cause relative movement between body 182 and gear rack 184 such that member 20, coupling member 180, body 182, extender 202 and fastener 216 axially translate as one unit.

Handle 158 is engaged to shaft 16 of rack 14 and rotated, in the directions shown by arrows G in FIG. 12, such that member 20 with coupling member 180, body 182, extender 202 and fastener 216 axially translate along shaft 16, in the directions shown by arrows H in FIG. 12, relative to rack 14, to apply a distraction or compression force to vertebrae. Member 20 axially translates relative to member 14 such that body 182 axially translates relative to body 120. Relative translation of bodies 120, 182 causes fasteners 210, 216, which are connected to bodies 120, 182 via extenders 128, 202, to substantially axially compress or distract vertebra V1 and vertebra V3 to restore vertebral body height of vertebrae V to treat the fracture of vertebra V2.

Shaft 148 is oriented in the first non-locking orientation so that body 120 translates along gear rack 68 along arcuate path P1 as shaft 148 rotates, as described herein. Handle 158 is rotated, in the directions shown by arrows J in FIG. 12, such that body 120 translates along arcuate path P1 along gear rack 68 relative to member 14. Relative translation of body 120 along arcuate path P1 rotates fastener 210, which is connected to body 120 via extender 128, at a center of rotation from body 120 corresponding to radius R1. Fastener 210 rotates, as shown by arrows Q, to rotate vertebra V1 to achieve lordosis and restore curvature of vertebrae V to treat the fracture of vertebra V2.

Shaft 208 is oriented in the first non-locking orientation so that body 182 translates along gear rack 184 along arcuate path P2 as shaft 208 rotates, as described herein. Handle 157 is rotated, in the directions shown by arrows W in FIG. 12, such that body 182 translates along arcuate path P2 along gear rack 184 relative to member 20. Relative translation of body 182 along arcuate path P2 rotates fastener 216, which is connected to body 182 via extender 202, at a center of rotation from body 182 corresponding to radius R2. Fastener 216 rotates, as shown by arrows K, to rotate vertebra V3 to achieve lordosis and restore curvature of vertebrae V to treat the fracture of vertebra V2. In some embodiments, this configuration of instrument 12 compresses and/or distracts vertebra V to restore vertebral body height and restores curvature of vertebrae V by rotating vertebra about a center of rotation corresponding to a bone fastener adjacent a facet joint.

Upon completion of a procedure, as described herein, the surgical instruments, assemblies and non-implanted components of spinal correction system 10 are removed and the incision(s) are closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10. In some embodiments, spinal correction system 10 may include one or a plurality of plates, connectors and/or bone fasteners for use with a single vertebral level or a plurality of vertebral levels.

In some embodiments, one or more of fasteners 210, 216 may be engaged with tissue in various orientations, such as, for example, series, parallel, offset, staggered and/or alternate vertebral levels. In some embodiments, one or more of fasteners 210, 216 may comprise multi-axial screws, sagittal angulation screws, pedicle screws, mono-axial screws, uniplanar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the components and/or surfaces of spinal correction system 10 with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 13-19, system 10, similar to the systems and methods described with regard to FIGS. 1-12, comprises an instrument 312, similar to instrument 12 described herein. Instrument 312 is configured for engagement with spinal constructs to axially and angularly correct a spinal disorder, such as, for example, trauma and/or fracture of vertebrae, which may include a sagittal deformity, as described herein. Instrument 312 includes a member, such as, for example, a compression and distraction rack 314 defining a longitudinal axis A2. Rack 314 has a non-uniform cross section configuration for disposal in correspondingly shaped passageways of a member 320 and a member 460, as described herein. Rack 314 includes a semi-circular section 316 extending along its length. Section 316 has an arcuate outer surface 318 having an external thread form engageable with member 320, as described herein. Rack 314 includes an elongate member 322 extending along its length and projecting from a substantially planar surface 324 of section 316. In some embodiments, the external thread form may include a single thread turn or a plurality of discrete threads. In some embodiments, rack 314 has a variously configured cross section configuration, such as, for example, oval, oblong, triangular, rectangular, square, polygonal, irregular, uniform, non-uniform, variable and/or tapered.

Instrument 312 includes member 320. Member 320 is disposed with rack 314 and is axially translatable along rack 314 along longitudinal axis A2. Member 320 has a substantially square-shaped configuration. In some embodiments, member 320 is variously configured, such as, for example, oval, oblong, triangular, rectangular, polygonal, irregular, uniform, non-uniform, variable and/or tapered. Member 320 includes a centrally disposed fastener, such as, for example, a hex nut 326. Hex nut 326 is configured for engagement with a nut reducer 328 such that hex nut 326 is rotatable relative to member 320. Hex nut 326 includes an inner threaded surface 330 engageable with outer surface 318 of rack 314 such that as hex nut 326 rotates, member 320 translates along longitudinal axis A2 and applies an axial distracting force on vertebrae at head 212 of fastener 210, as described herein. Surface 330 defines an inner passageway 332 configured for disposal of rack 314. In some embodiments, member 320 includes a lock (not shown), similar to lock 56 described with regard to FIGS. 1-12.

Figure 16:
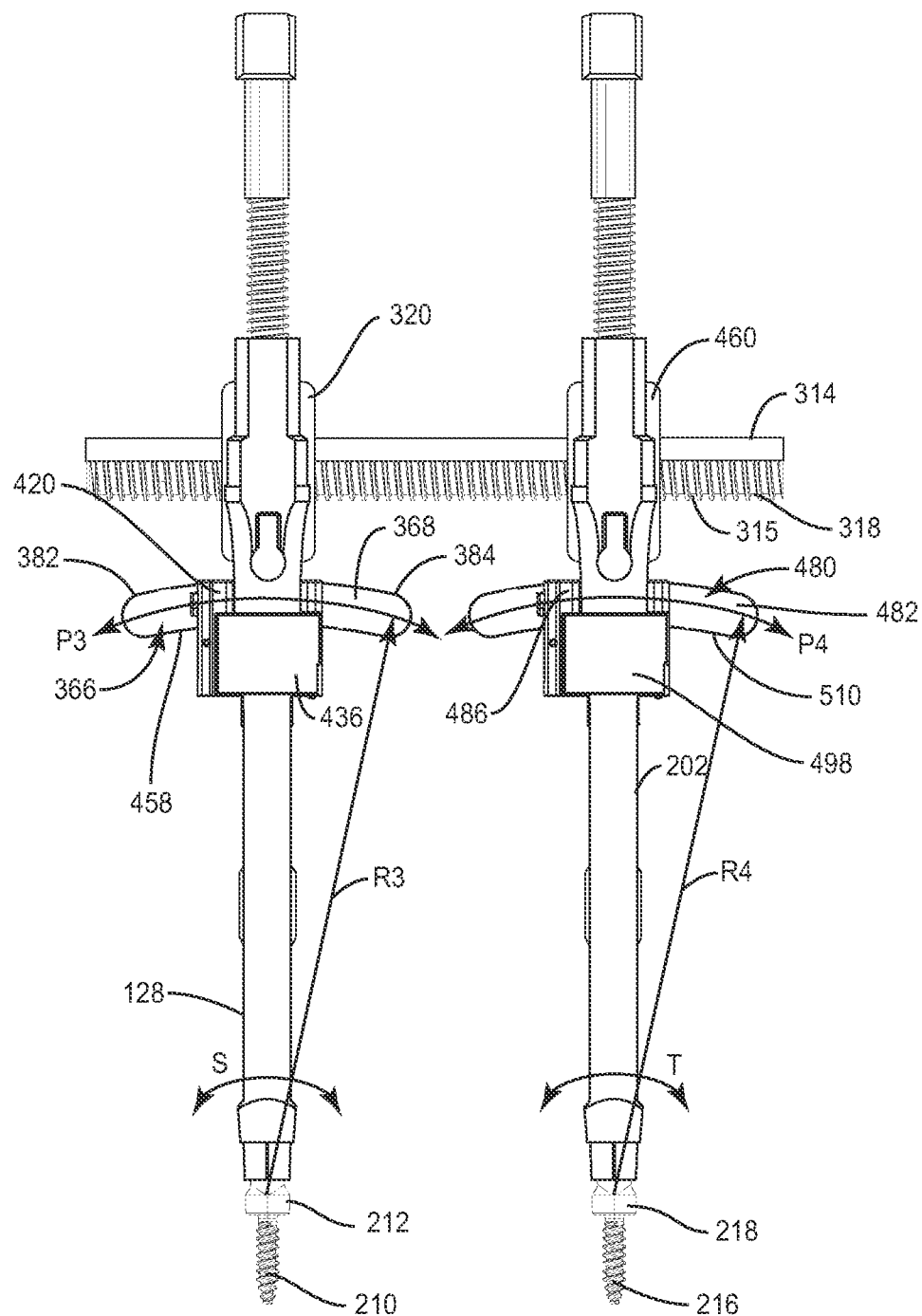
FIG. 16 is a plan view of components of the system shown in FIG. 13.
Figure 19:
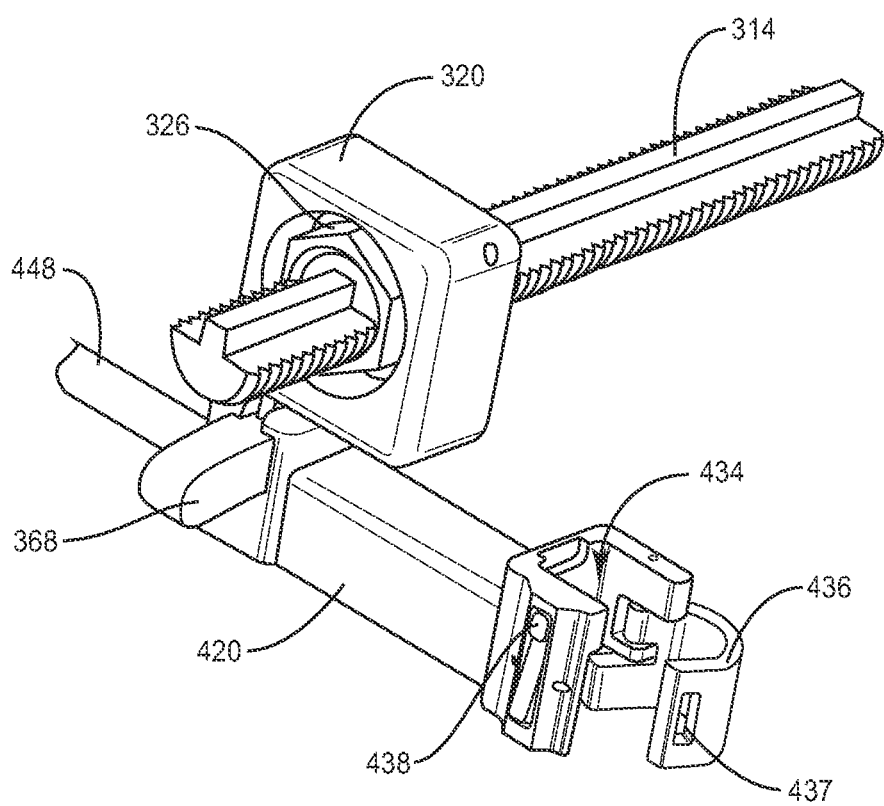
FIG. 19 is a perspective view of components of the system shown in FIG. 13.

Instrument 312 includes a coupling member 366. Coupling member 366 is disposed with member 320 and a body 420, as described herein. Coupling member 366 includes a portion, such as, for example, a gear rack 368, similar to gear rack 68 described herein, and a portion, such as, for example, a post 370, similar to post 70 described herein. Coupling member 366 is integrally connected to or monolithically formed with member 320. In some embodiments, coupling member 366 is connected to member 320 by various fastening engagements, such as, for example, hinged engagement, frictional engagement, threaded engagement, mutual grooves, screws and/or nails. Gear rack 368 extends between an end 382 and an end 384. Gear rack 368 has an arcuate configuration between ends 382, 384 having a radius of curvature R3, as shown in FIG. 16, defining an arcuate path P3, similar to radius of curvature R1 and arcuate path P1 described with regard to FIGS. 1-12. Gear rack 368 includes a lower surface 458 having a toothed outer surface (not shown), similar to toothed outer surface 88 of gear rack 68 described herein. Gear rack 368 is disposed with body 420 such that body 420 is translatable along arcuate path P3 between ends 382, 384 of gear rack 368.

Instrument 312 includes body 420, similar to body 120 described herein with regard to FIGS. 1-12. Body 420 is connected to member 320 via coupling member 366. Body 420 is translatable along arcuate path P3 relative to gear rack 368 to rotate extender 128 attached to fastener 210. Body 420 translates along path P3 and rotates about a center of rotation, such as, for example, from radius R3, which corresponds to a portion of fastener, such as, for example, the connection of head 212 and shaft 214. As such, translation of body 420 along path P3 rotates fastener 210, in the direction shown by arrow S in FIG. 16, to rotate vertebra to achieve lordosis and restore curvature of a spine during treatment of a disorder such as trauma, which may include correction of a sagittal deformity, as described herein.

Body 420 extends between an end 422 and an end 424 defining a longitudinal axis A3. End 422 includes an inner surface 426 defining a cavity 428 extending transverse to axis A3. Cavity 428 has a cross section configuration configured for disposal of gear rack 368 such that body 420 is translatable between end 382 and end 384 of gear rack 368. End 422 includes two opposing flanges 430 extending into cavity 428 to capture gear rack 368 in cavity 428 such that movement of body 420 other than along arcuate path P3 is resisted and/or prevented.

End 424 defines a cavity 434 configured for disposal of an implant support, such as, for example, extender 128 described herein. End 424 includes a capture element, such as, for example, a clip 436, similar to clip 130 described herein, to engage extender 128. Clip 436 is releasably engageable with end 424 via a button 438. In the engaged position, a latch (not shown) of button 438 engages an opening 437 of clip 436 to enclose extender 128 and capture extender 128 in cavity 434. End 424 includes a protrusion, such as, for example, a boss 440 configured for disposal in an opening (not shown) in extender 128 such that movement of extender 128 within cavity 434 is resisted and/or prevented. Body 420 includes a lock 356, similar to lock 140 described herein with regard to FIGS. 1-12, disposed between ends 422, 424.

Body 420 includes a rotatable shaft 448, similar to shaft 148 described herein with regard to FIGS. 1-12. Shaft 448 is translatable within body 420 along longitudinal axis A3 between a first non-locking orientation, a second non-locking orientation and a locking orientation, similar to the first non-locking orientation, the second non-locking orientation and the locking orientation described herein with regard to FIGS. 1-12. Shaft 448 extends between an end 454 and an end 456. End 454 is configured for releasable engagement with handle 158 to actuate the rotation of shaft 448. End 456 of shaft 448 has a gear portion (not shown), similar to gear portion 160 of shaft 148 described herein, engageable with lower surface 458 of gear rack 368 such that as shaft 448 rotates, body 420 translates along arcuate path P3 relative to gear rack 368 to apply a rotational force to vertebrae at head 212 of fastener 210.

Instrument 312 includes a member 460, similar to member 320 described herein. Member 460 includes an inner surface 462 engageable with rack 314. Inner surface 462 defines a passageway 464 having a cross section configuration correspondingly shaped for disposal of rack 314 such that relative rotation between inner surface 462 and rack 314 is resisted and/or prevented. Member 460 includes a lock 466, similar to lock 56 described herein with regard to FIGS. 1-12, which resists and/or prevents axial translation of member 460 relative to rack 314. Lock 466 is configured to selectively fix member 460 relative to rack 314. Lock 466 includes a button 468 and a lower portion 470 coupled to button 468. Lower portion 470 is disposable in a space 315 defined between threads of outer surface 318 of rack 314. Lock 466 is resiliently biased to a locking orientation such that lower portion 470 is engaged with outer surface 318 of rack 314 and the axial translation of member 460 along rack 314 is resisted and/or prevented. To orient lock 466 from the locking orientation to the non-locking orientation, a force is applied to button 468, in the direction shown by arrow L in FIG. 17, to disengage lower portion 470 from rack 314 such that member 460 is translatable along rack 314.

Instrument 312 includes a coupling member 480, similar to coupling member 366 described herein. Coupling member 480 is disposed with member 460 and a body 486, to be described herein. Coupling member 480 includes a portion, such as, for example, a gear rack 482, similar to gear rack 368 described herein, and a portion, such as, for example, a post 484, similar to post 370 described herein. Coupling member 480 is integrally connected to or monolithically formed with member 460. Gear rack 482 has an arcuate configuration having a radius of curvature R4 defining an arcuate path P4, similar to radius of curvature P3 and arcuate path P3 described herein. Gear rack 482 is disposed with body 486 such that body 486 is translatable along arcuate path P4.

Instrument 312 includes body 486, similar to body 420 described herein. Body 486 is connected to member 460 via coupling member 480. Body 486 is translatable along arcuate path P4 relative to gear rack 482 to rotate extender 202 about fastener 216 to correct a sagittal deformity. Body 486 extends between an end 488 and an end 490 defining a longitudinal axis A4. End 488 includes an inner surface 492 defining a cavity 494 extending transverse to axis A4, similar to cavity 428 described herein. Cavity 494 has a cross section configuration configured for disposal of gear rack 482 such that body 486 is translatable between opposite ends of gear rack 482.

End 490 defines a cavity 496, similar to cavity 434 described herein, configured for disposal of an implant support, such as, for example, extender 202 described herein. End 490 includes a capture element, such as, for example, a clip 498, similar to clip 436 described herein, to engage extender 202. End 490 includes a protrusion, such as, for example, a boss 500 configured for disposal in an opening (not shown) in extender 202. Body 486 includes a lock 502, similar to lock 140 described herein with regard to FIGS. 1-12, disposed between ends 488, 490.

Body 486 includes a rotatable shaft 504, similar to shaft 448 described herein. Shaft 504 extends between an end 506 and an end 508. End 506 is configured for releasable engagement with handle 158 to actuate the rotation of shaft 504. End 508 of shaft 504 is engaged to a lower surface 510 of gear rack 482 such that as shaft 504 rotates, body 486 translates along the arcuate path relative to gear rack 482 to apply a rotational force to vertebrae at head 218 of fastener 216.

In operation, to treat a spine disorder, such as, for example, trauma of the spine, instrument 312 is manipulated for engagement with extenders 128, 202 such that fasteners 210, 216 are movable from a first configuration, which may include fasteners 210, 216 being disposed in an initial axial position and in an initial angle relative to one another and a second configuration, which may include fasteners 210, 216 being disposed at a corrected axial position and angle relative to one another. In some embodiments, instrument 312 is employed to treat vertebrae such that selected vertebra can be relatively translated for substantially axial compression or distraction to restore vertebral body height and rotated to achieve lordosis and restore curvature of the spine.

Instrument 12 is disposed adjacent a surgical site and manipulated for engagement with fasteners 210, 216 via extenders 128, 202 such that vertebrae can be axially distracted. Extenders 128, 202 are disposed in cavities 434, 496 of bodies 420, 486 such that bosses 440, 500 are disposed in openings (not shown) in extenders 128, 202, respectively. Clips 436, 498 are engaged to ends 424, 490 of bodies 420, 486 to capture extenders 128, 202 in cavities 434, 496, respectively.

To orient members 320, 460 relative to one another such that extenders 128, 202 are in alignment with a first vertebral body and a second vertebral body, a force is applied to button 468, in the direction shown by arrow L in FIG. 17, to disengage lower portion 470 from rack 314 such that member 460 is translatable along rack 314. With lock 466 in the non-locking orientation, member 460 is translated along rack 314.

Figure 13:
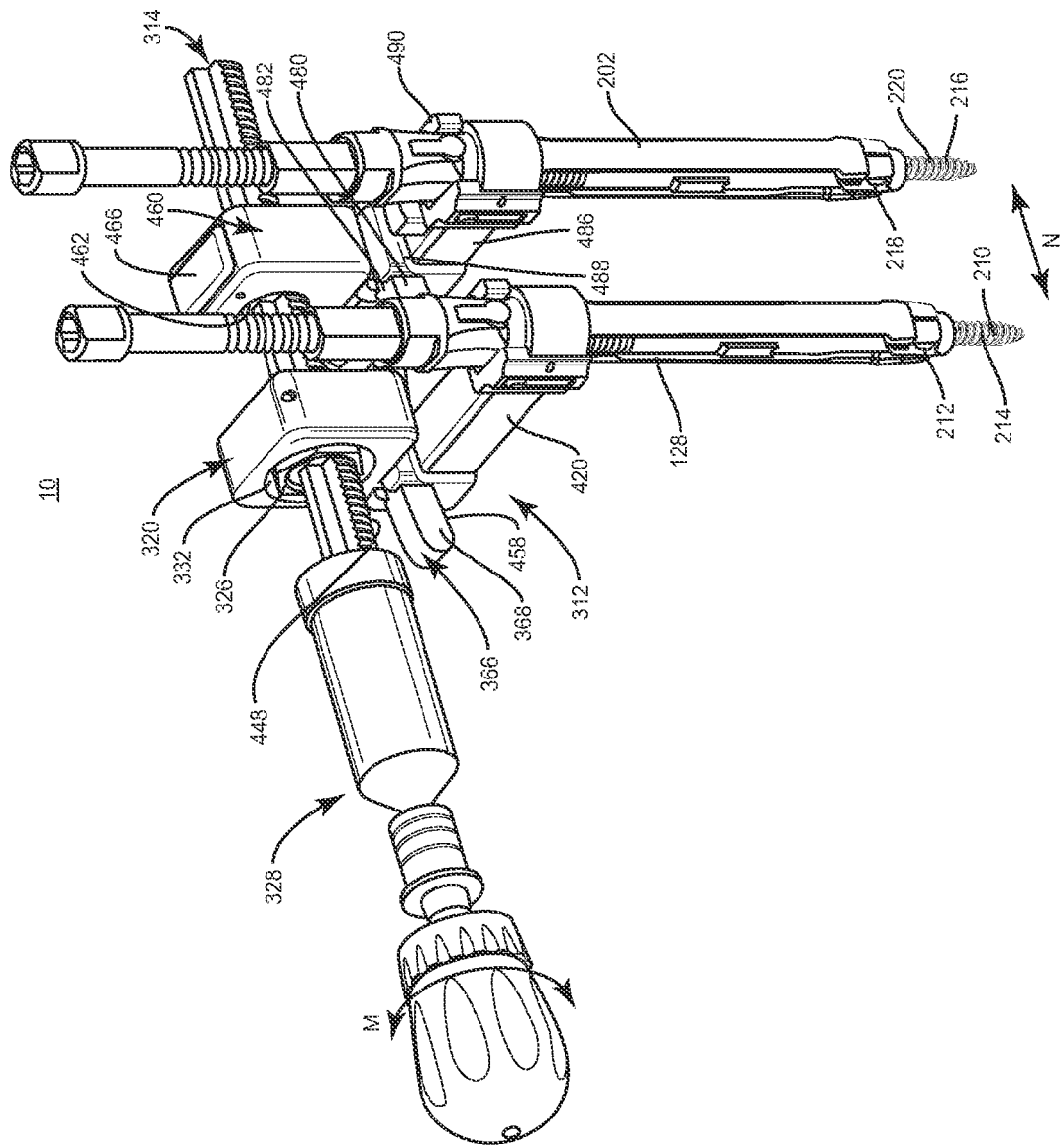
FIG. 13 is a perspective view of components of one embodiment of a spinal correction system in accordance with the principles of the present disclosure.
Figure 14:
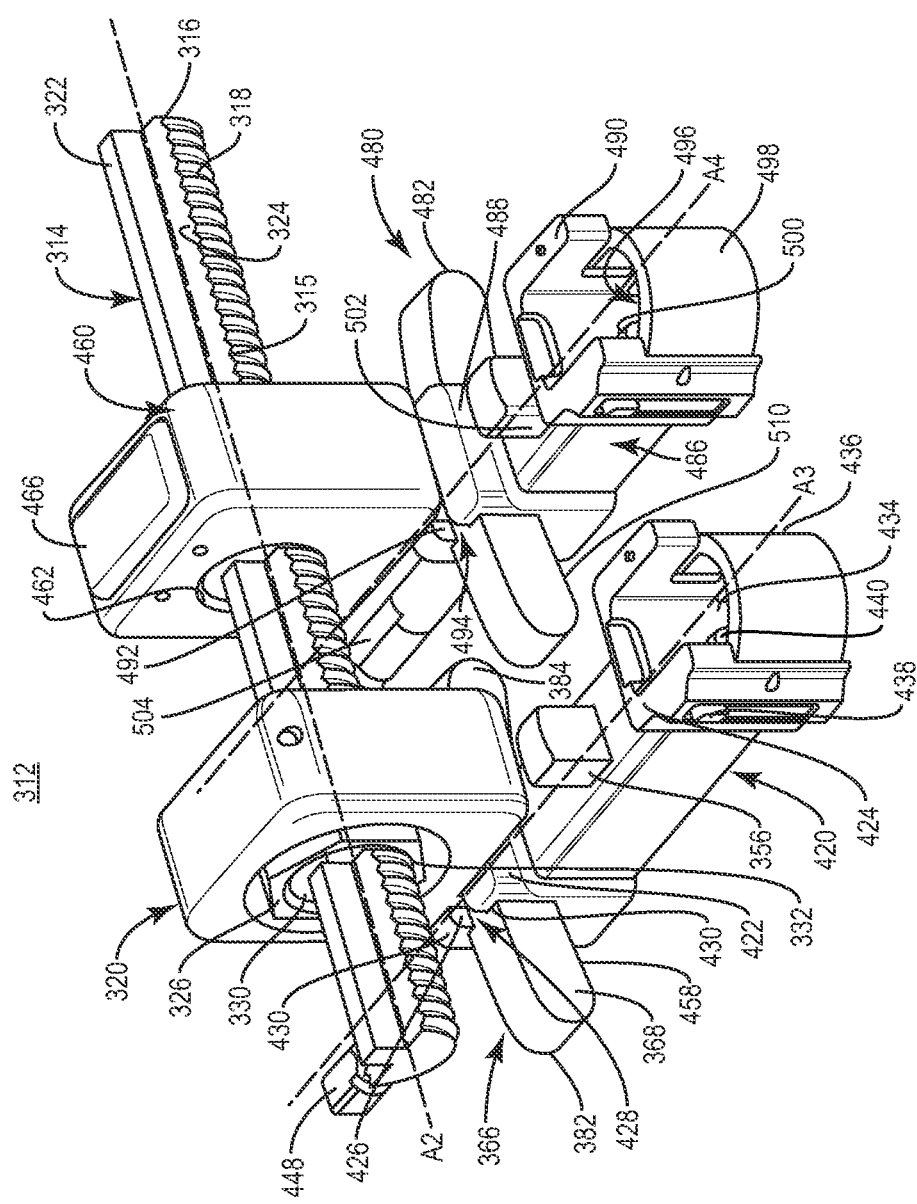
FIG. 14 is a perspective view of components of the system shown in FIG. 13.
Figure 15:
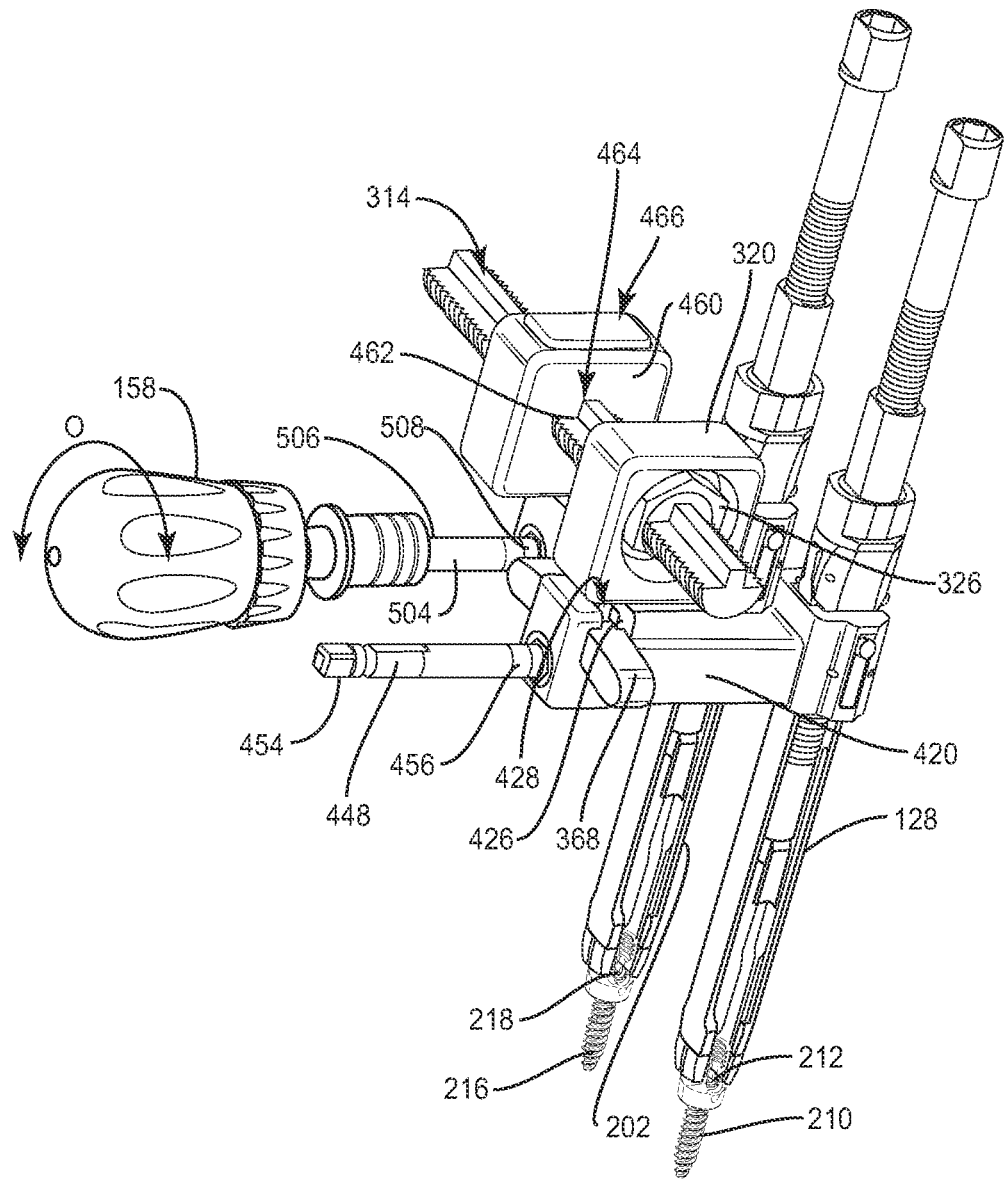
FIG. 15 is a perspective view of components of the system shown in FIG. 13.

To apply a compression or distraction force to vertebrae, nut reducer 328 is engaged to hex nut 326 and rotated, in the directions shown by arrows M in FIG. 13, such that member 320 axially translates along rack 314 in axis A2. Extender 202 with fastener 216 axially translates, in the directions shown by arrows N in FIG. 13, as member 320 axially translates in axis A2 to apply a distracting or compressing force to vertebrae to restore vertebral body height. Member 320 axially translates relative to member 460 such that body 420 axially translates relative to body 486. Relative translation of bodies 420, 486 causes fasteners 210, 216, which are connected to bodies 420, 486 via extenders 128, 202, to substantially axially compress or distract the first vertebral body and the second vertebral body to restore vertebral body height of the vertebrae to treat the fracture to the vertebrae.

To apply a rotational force to vertebrae, shaft 448 is oriented in the first non-locking orientation so that body 420 translates along gear rack 368 along arcuate path P3 as shaft 448 rotates, as described herein. Handle 158 is rotated, in the directions shown by arrows O in FIG. 15, such that body 420 translates along arcuate path P3 along gear rack 368 relative to member 320. Relative translation of body 420 along arcuate path P3 rotates fastener 210, which is connected to body 420 via extender 128, at a center of rotation from body 420 corresponding to radius R3. Fastener 210 rotates, as shown by arrows S in FIG. 16, to rotate vertebra to achieve lordosis and restore curvature of vertebrae to treat a fracture of vertebra. Shaft 504 is oriented in the first non-locking orientation to engage the gear portion (not shown) of shaft 504 with the toothed outer surface (not shown) of gear rack 482. With shaft 504 being positioned in the first non-locking orientation, handle 158 is rotated, in the directions shown by arrows O in FIG. 15, such that body 486 translates along arcuate path P4 along gear rack 482 relative to member 460. Relative translation of body 486 along arcuate path P4 rotates fastener 216, which is connected to body 486 via extender 202, at a center of rotation from body 486 corresponding to radius R4. Fastener 216 rotates, as shown by arrows T in FIG. 16, to rotate vertebra to achieve lordosis and restore curvature of vertebrae to treat a fracture of vertebra. In some embodiments, this configuration of instrument 312 compresses and/or distracts vertebrae to restore vertebral body height and restores curvature of vertebrae by rotating vertebra about a center of rotation corresponding to a bone fastener adjacent a facet joint.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a first member defining a longitudinal axis;
a second member disposed with the first member and being axially translatable relative to the first member;
a first body connected to the first member and being translatable along an arcuate path relative to the first member, the first body being connected to a first implant support;
a second body connected to the second member and being translatable along an arcuate path relative to the second member, the second body being connected to a second implant support; and
a first gear rack disposed with the first member and the first body such that the first body is translatable along the arcuate path,
wherein the rack defines a first cavity disposed on a first lateral side and a second cavity disposed on a second lateral side and the first body includes opposing flanges configured for mating engagement with the first and second cavities.

2. A surgical instrument as recited in claim 1, wherein the flanges extend from a female mating part having an inner surface defining a passageway and the cavities extend into a male mating part configured for mating engagement with the inner surface.

3. A surgical instrument as recited in claim 1, further comprising a second gear rack disposed with the second member and the second body such that the second body is translatable along the arcuate path.

4. A surgical instrument as recited in claim 1, wherein the first rack includes a toothed outer surface and the first body includes a rotatable shaft having a gear portion configured for mating engagement with the toothed outer surface to translate the first body along the rack.

5. A surgical instrument as recited in claim 4, wherein the shaft is axially translatable within a cavity defined by the first body between a first position such that the gear portion engages the toothed outer surface and a second position such that the first body is translatable along the arcuate path.

6. A surgical instrument as recited in claim 1, further comprising a coupling member including a first portion having an arcuate configuration and a second portion extending substantially perpendicularly from the first portion, the first portion being disposable with the first body and the second portion being disposable in an inner passageway defined in the first member.

7. A surgical instrument as recited in claim 6, wherein the second portion is connected to the first portion via a hinge.

8. A surgical instrument as recited in claim 6, wherein the inner passageway includes a tapered configuration and the second portion is disposable in a friction fit engagement with the first member.

9. A surgical instrument as recited in claim 8, wherein the second portion is translatable along the inner passageway in a first direction and a second opposing direction, the second portion including a bearing configuration to resist translation in the first direction.

10. A surgical instrument as recited in claim 1, wherein the second member includes a lock that resists axial translation of the second member relative to the first member.

11. A surgical instrument as recited in claim 10, wherein the lock is resiliently biased to a locking orientation.

12. A surgical instrument as recited in claim 1, wherein the first member includes a threaded shaft and the second member includes an inner threaded surface engageable with the shaft.

13. A surgical instrument as recited in claim 1, wherein the first member includes a gear rack and the second member includes an inner threaded surface engageable with the gear rack, and further comprising a third member including an inner surface engageable with the gear rack such that as the inner threaded surface of the second member rotates relative to the gear rack, the second member linearly translates along the gear rack.

14. A surgical instrument as recited claim 1, wherein at least one of the bodies include a capture element to engage the implant support.

15. A surgical instrument as recited in claim 14, wherein the capture element is releasably engageable with the at least one of the bodies.

16. A surgical instrument comprising:
a first member including a linear shaft;
a second member being axially translatable along the shaft and including a lock configured to selectively fix the second member relative to the first member;
a first gear rack having an arcuate configuration and being disposable with the first member;
a first body including a gear portion connected with the first gear rack and being translatable along the first gear rack in an arcuate path and relative to the first member, the first body including a lock configured to selectively fix the first body relative to the first gear rack and defining a cavity configured for disposal of a first implant support;
a second gear rack having an arcuate configuration and being disposable with the second member; and
a second body including a gear portion connected with the second gear rack and being translatable along the second gear rack in an arcuate path and relative to the second member, the second body including a lock configured to selectively fix the second body relative to the second gear rack and defining a cavity configured for disposal of a second implant support.

17. A surgical instrument as recited claim 16, wherein at least one of the bodies include a capture element to engage the implant support.

18. A surgical instrument comprising:
a first member defining a longitudinal axis and including a gear rack;
a second member disposed with the first member and being axially translatable relative to the first member, the second member including an inner threaded surface engageable with the gear rack;
a third member including an inner surface engageable with the gear rack such that as the inner threaded surface of the second member rotates relative to the gear rack, the second member linearly translates along the gear rack;
a first body connected to the first member and being translatable along an arcuate path relative to the first member, the first body being connected to a first implant support; and
a second body connected to the second member and being translatable along an arcuate path relative to the second member, the second body being connected to a second implant support.

19. A surgical instrument as recited claim 18, further comprising a coupling member including a first portion having an arcuate configuration and a second portion extending substantially perpendicularly from the first portion, the first portion being disposable with the first body and the second portion being disposable in an inner passageway defined in the first member.

20. A surgical instrument as recited claim 19, wherein the second portion is connected to the first portion via a hinge.

\* \* \* \* \*